(12) United States Patent
Imura et al.

(10) Patent No.: US 11,428,631 B2
(45) Date of Patent: Aug. 30, 2022

(54) METHOD FOR MEASURING SPECTRAL RADIATION CHARACTERISTICS OF FLUORESCENCE WHITENED SAMPLE, AND DEVICE FOR MEASURING SPECTRAL RADIATION CHARACTERISTICS OF FLUORESCENCE WHITENED SAMPLE

(71) Applicant: KONICA MINOLTA, INC., Chiyoda-ku (JP)

(72) Inventors: Kenji Imura, Mishima (JP); Yoshiroh Nagai, Nishinomiya (JP)

(73) Assignee: KONICA MINOLTA, INC., Tokyo (JP)

( * ) Notice: Subject to any disclaimer, the term of this patent is extended or adjusted under 35 U.S.C. 154(b) by 595 days.

(21) Appl. No.: 16/492,845

(22) PCT Filed: Mar. 1, 2018

(86) PCT No.: PCT/JP2018/007824
§ 371 (c)(1),
(2) Date: Sep. 10, 2019

(87) PCT Pub. No.: WO2018/173680
PCT Pub. Date: Sep. 27, 2018

(65) Prior Publication Data
US 2021/0140884 A1 May 13, 2021

(30) Foreign Application Priority Data

Mar. 21, 2017 (JP) .............................. JP2017-054885

(51) Int. Cl.
*G01N 21/64* (2006.01)
*G01N 33/34* (2006.01)
*G01J 3/44* (2006.01)

(52) U.S. Cl.
CPC ........ *G01N 21/6428* (2013.01); *G01J 3/4406* (2013.01); *G01N 33/346* (2013.01);
(Continued)

(58) Field of Classification Search
CPC ............... G01N 21/64; G01N 21/6428; G01N 2201/062; G01N 2021/6417;
(Continued)

(56) References Cited

U.S. PATENT DOCUMENTS 5,384,641 A * 1/1995 Imura .................. G01N 21/474
250/228
6,020,959 A * 2/2000 Imura .................. G01J 3/0254
250/461.1
(Continued)

FOREIGN PATENT DOCUMENTS

JP     H 8 313349     11/1996
JP     2000-230861     8/2000
(Continued)

*Primary Examiner* — Jermele M Hollington
*Assistant Examiner* — Suresh K Rajaputra
(74) *Attorney, Agent, or Firm* — Cozen O'Connor

(57) ABSTRACT

An approximation B'f(Id,λ) of a fluorescence spectral emissivity coefficient by a standard illumination light Id is obtained at following steps from spectral power distributions R(Ik,λ) of sample radiation lights radiated from a fluorescence whitened sample when the fluorescence whitened sample is sequentially illuminated with a plurality of excitation lights Ik having different spectral power distributions, and a spectral power distribution Id(λ) of the standard illumination light Id. Spectral power distributions Rf(Ik,λ) of fluorescence are obtained from the spectral power distributions R(Ik,λ) by respective excitation lights Ik (first step). The spectral power distributions Rf(Ik,λ) of fluorescence by the respective excitation lights Ik are linearly combined with a given weighting coefficient Wk, and an approximation R'f(Id,λ) of a spectral power distribution of fluorescence by
(Continued)

the standard illumination light Id is obtained by equation (second step: #11). From the approximation R'f(Id,λ) and the spectral power distribution Id(λ) of the standard illumination light Id, the approximation B'f(Id,λ) is obtained by equation (third step: #12).

34 Claims, 15 Drawing Sheets

(52) U.S. Cl.
CPC ................ *G01N 2021/6417* (2013.01); *G01N 2201/062* (2013.01); *G01N 2201/065* (2013.01)

(58) Field of Classification Search
CPC ........... G01N 2201/065; G01N 21/274; G01N 21/255; G01N 33/34; G01N 33/346; G01J 3/4406; G01J 3/0254; G01J 3/0218
See application file for complete search history.

(56) References Cited

U.S. PATENT DOCUMENTS

2008/0137086 A1* 6/2008 Imura .................. G01N 21/251
356/433
2009/0242803 A1* 10/2009 Imura .................. G01N 21/645
250/578.1

FOREIGN PATENT DOCUMENTS

JP       2006-292510       10/2006
JP       2009-236486       10/2009

* cited by examiner

FIG. 3
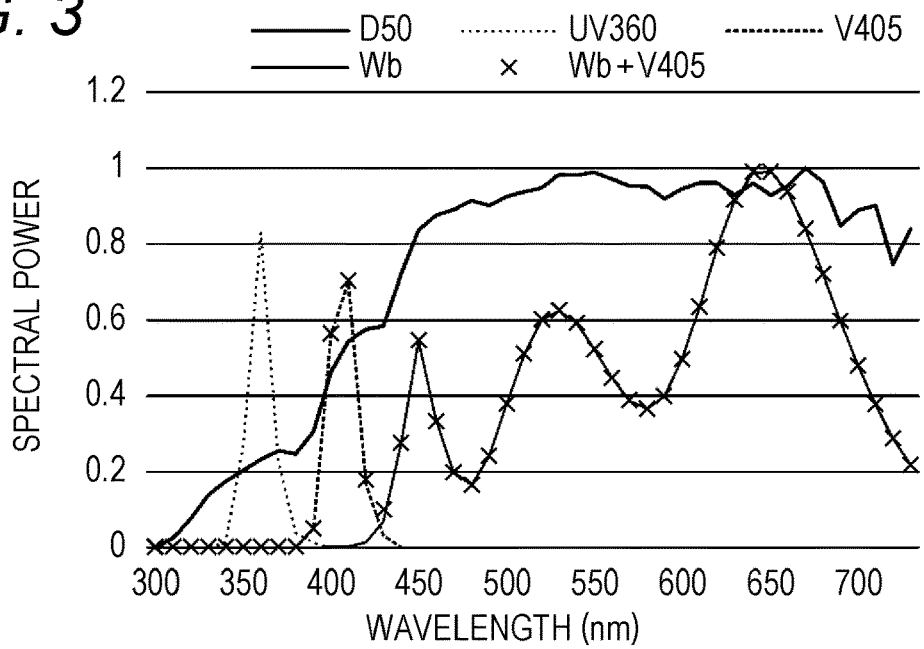
FIG. 4
| TYPE T | CORRESPONDING FLUORESCENCE WHITENED PAPER |
|---|---|
| 1 | PAPER D |
| 2 | PAPER E |
| 3 | PAPER F, PAPER B |
| 4 | PAPER G, PAPER A, PAPER C |
FIG. 5
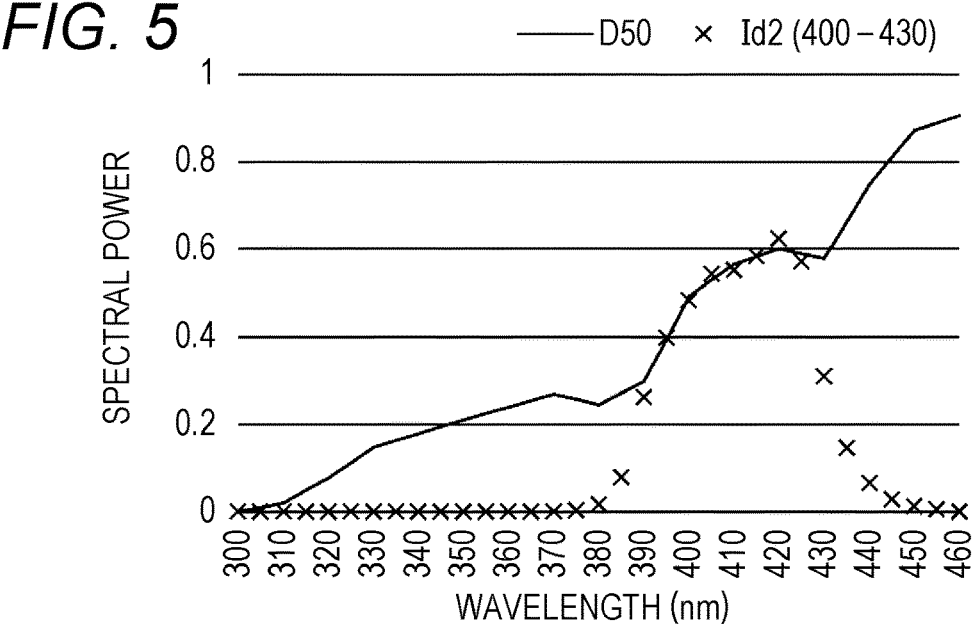

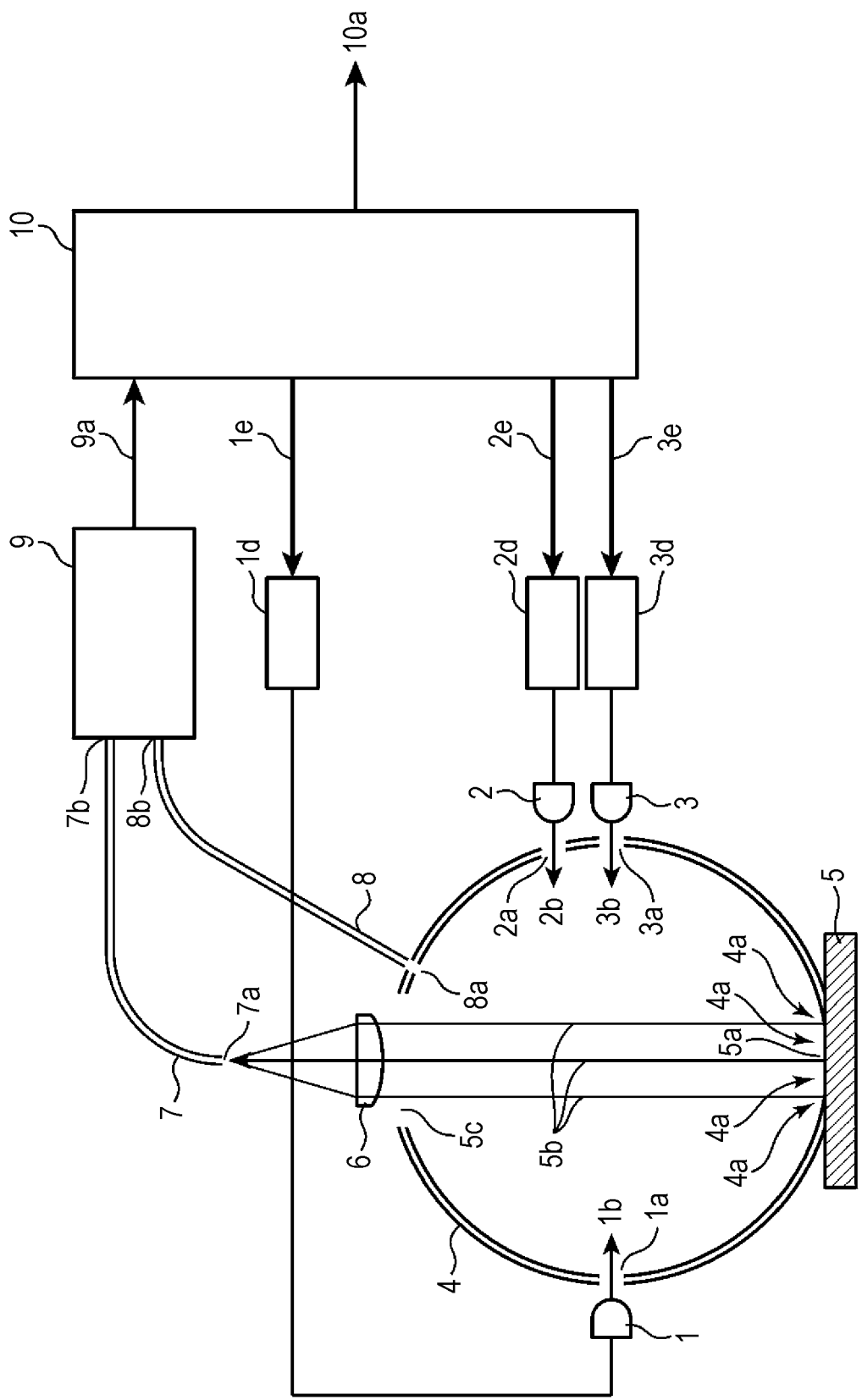

PAPER A

PAPER G

METHOD FOR MEASURING SPECTRAL RADIATION CHARACTERISTICS OF FLUORESCENCE WHITENED SAMPLE, AND DEVICE FOR MEASURING SPECTRAL RADIATION CHARACTERISTICS OF FLUORESCENCE WHITENED SAMPLE

RELATED APPLICATIONS

This is a U.S. National Phase Application under 35 USC 371 of International Application PCT/JP2018/007824 filed on Mar. 1, 2018.

This application claims the priority of Japanese application no. 2017-054885 filed Mar. 21, 2017, the entire content of which is hereby incorporated by reference.

TECHNICAL FIELD

The present invention relates to a technology of measuring spectral radiation characteristics of a fluorescence whitened sample.

BACKGROUND ART

A total spectral emissivity coefficient $B_t(I,\lambda)$ represented by following equation (1) is used for measuring a color of the sample. The total spectral emissivity coefficient $B_t(I,\lambda)$ is one of indices indicating the spectral radiation characteristics of the sample. In a case of the fluorescence whitened sample, a radiation light thereof is the sum of a reflected light and fluorescence, so that the total spectral emissivity coefficient $B_t(I,\lambda)$ of the fluorescence whitened sample is represented by following equation (2). $B_r(\lambda)$ represents a spectral reflectivity coefficient. $B_f(I,\lambda)$ represents a fluorescence spectral emissivity coefficient. Note that, in this specification, subscripts are used in mathematical expressions, and the subscripts are not used except for the mathematical expressions, but both have the same meaning (this is also applicable in claims). For example, although "t" included in equation (1) is a subscript, this is a normal character in the specification ($Bt(I,\lambda)$), and both have the same meaning.

A standard illumination light is required to obtain the total spectral emissivity coefficient $B_t(I,\lambda)$ of the fluorescence whitened sample. At present, although there is a light source of an illumination light that approximates the standard illumination light, a light source of the standard illumination light is not yet put into practical use.

Therefore, an approximation $B't(I,\lambda)$ of the total spectral emissivity coefficient $B_t(I,\lambda)$ of the fluorescence whitened sample is obtained by an approximate measuring method. The conventional approximate measuring method obtains $B't(I,\lambda)$ using a specific bispectral fluorescence emissivity coefficient. For this reason, in a case where the fluorescence whitened sample the color of which is to be measured has a bispectral fluorescence emissivity coefficient different from the specific bispectral fluorescence emissivity coefficient, it is not possible to obtain a highly accurate approximation $B't(I,\lambda)$.

The above-described details are hereinafter described until the object of the invention. Note that, an outline of the embodiment is described at the beginning of the "Description of embodiments".

Color characteristics of the sample are obtained using the total spectral emissivity coefficient. A radiation light from the sample illuminated and receiving light under a certain condition is set as a first radiation light, and a radiation light from a completely diffusing reflective surface (ideal white surface) illuminated and receiving light under the same condition is set as a second radiation light. The total spectral emissivity coefficient is a ratio between the first radiation light and the second radiation light for each wavelength. A reflectivity of the completely diffusing reflective surface is 1 over all the wavelengths, so that the total spectral emissivity coefficient is expressed by following equation (1) except for a proportional constant. $Bt(I,\lambda)$ is the total spectral emissivity coefficient by an illumination light I. $Rt(I,\lambda)$ is a spectral power distribution (SPD) of a sample radiation light by the illumination light I. $I(\lambda)$ is a spectral power distribution of the illumination light I.

[Math. 1]

$$B_t(I, \lambda) = \frac{R_t(I, \lambda)}{I(\lambda)} \qquad \text{Equation (1)}$$

Today, most of printing paper is whitened with a fluorescence whitening agent (FWA) which converts components from ultraviolet to purple ranges of the illumination light into blue-range fluorescence. The radiation light of a fluorescence sample is the sum of the reflected light and the fluorescence. Therefore, as illustrated in FIG. 20, the total spectral emissivity coefficient $Bt(I,\lambda)$ of the fluorescence whitened sample is the sum of the spectral reflectivity coefficient $Br(\lambda)$ and the fluorescence spectral emissivity coefficient $Bf(I,\lambda)$. The spectral reflectivity coefficient $Br(\lambda)$ is a ratio for each wavelength between the reflected light from the sample illuminated and receiving light under a certain condition and the radiation light from the completely diffusing reflective surface illuminated and receiving light under the same condition. The fluorescence spectral emissivity coefficient $Bf(I,\lambda)$ by the illumination light I is a ratio for each wavelength between fluorescence from the sample illuminated and receiving light under a certain condition and the radiation light from a completely diffusing reflective surface illuminated and receiving light under the same condition. Therefore, the total spectral emissivity coefficient $Bt(I,\lambda)$ of the fluorescence whitened sample may be expressed by following equation (2).

[Math. 2]

$$B_t(I,\lambda)=B_r(\lambda)+B_f(I,\lambda) \qquad \text{Equation (2)}$$

The spectral reflectivity coefficient $Br(\lambda)$ does not depend on the illumination light, but the fluorescence spectral emissivity coefficient $Bf(I,\lambda)$ provided by equations (3) and (4) depends on a bispectral fluorescence emissivity coefficient $F(\mu,\lambda)$ of the sample and a spectral power distribution $I(\mu)$ of the illumination light, so that the total spectral emissivity coefficient $Bt(I,\lambda)$ also depends on the spectral power distribution $I(\mu)$ of the illumination light. Here, $\mu$ represents an excitation wavelength included in a wavelength range of the illumination light, and $\lambda$ represents a fluorescence wavelength. Other than them (for example, $\lambda$ in equations (1) to (3)) represents a wavelength of the illumination light. Note that $Rf(I,\lambda)$ represents a spectral power distribution of fluorescence by the illumination light I.

[Math. 3]

$$B_f(I, \lambda) = \frac{R_f(I, \lambda)}{I(\lambda)} \qquad \text{Equation (3)}$$

[Math. 4]

$$R_f(I, \lambda) = \int I(\mu) F(\mu, \lambda) d\mu \qquad \text{Equation (4)}$$

Therefore, in a case where the color of the fluorescence whitened sample (for example, fluorescence whitened paper and a printing surface using this as a sheet of paper) is measured, it is necessary to define the spectral power distribution of the illumination light. As for paper, ISO 5631-1, 2, and 3 require standard illuminants C, D65, and D50 defined by CIE (International Commission on Illumination), respectively, and as for a printed matter, an M1 condition of ISO 13655 requires D50. That is, a measuring illumination light needs to have a relative spectral power distribution which approximates these standard illumination lights Id. However, since it is difficult to realize this practically, an approximate measuring method is generally used. As the approximate measuring method, there are, for example, a method of Görtner-Griesser, and a method of replacing this with numerical operation (for example, Patent Literatures 1 and 2). The contents of Patent Literatures 1 and 2 are described later. However, since all approximate measuring methods are based on a specific bispectral fluorescence emissivity coefficient, there is a fundamental disadvantage that the accuracy is deteriorated in a case where the measurement sample has the bispectral fluorescence emissivity coefficient deviating from the same.

On the other hand, in the paper manufacturing industry, a spectral reflectivity coefficient without a fluorescence whitening effect is often required. At present, in order to suppress fluorescence excitation, an ISO 2470 method for removing a component of 420 nm or shorter of the measuring illumination light is generally used. However, this method has a disadvantage that a reflectivity coefficient of 420 nm or shorter an effect of which on whiteness is not ignorable cannot be obtained.

The method of Patent Literature 1 is described. In this method, a fluorescence whitened sample x is illuminated with a first illumination light having a power in an ultraviolet range and a second illumination light having no power to obtain first and second total spectral emissivity coefficients Bt1($\lambda$) and Bt2($\lambda$) by the respective illumination lights, and the total spectral emissivity coefficients Bt1($\lambda$) and Bt2($\lambda$) are subjected to linear combination expressed by equation (5) by a weighting coefficient W($\lambda$) set for each wavelength in advance, thereby obtaining a synthetic spectral emissivity coefficient B't($\lambda$) approximating the total spectral emissivity coefficient of the sample illuminated with the standard illumination light.

[Math. 5]

$$B'_t(\lambda) = W(\lambda) \cdot B_{t1}(\lambda) + (1 - W(\lambda)) \cdot B_{t2}(\lambda) \qquad \text{Equation (5)}$$

The above-described weighting coefficient W($\lambda$) is set as follows. When a fluorescence reference sample having excitation/fluorescence characteristics approximating the sample is illuminated with the standard illumination light, the total spectral emissivity coefficient of the fluorescence reference sample is Bt($\lambda$). The fluorescence reference sample is illuminated with the first and second illumination lights, and the total spectral emissivity coefficients Bt1($\lambda$) and Bt2($\lambda$) by the respective illumination lights are measured. The weighting coefficient W($\lambda$) is set for each wavelength such that linear combination W($\lambda$)·Bt1($\lambda$)+(1−W($\lambda$))·Bt2($\lambda$) of Bt1($\lambda$) and Bt2($\lambda$) is equal to the spectral emissivity coefficient Bt($\lambda$).

The method of Patent Literature 2 is described. This method is basically the same as the method of Patent Literature 1, but the fluorescence reference sample is not used when setting the weighting coefficient W($\lambda$). According to the method of Patent Literature 2, a fluorescence spectral emissivity coefficient Bf1($\lambda$) by a first illumination light is calculated by using equations (3) and (4) from a predetermined bispectral fluorescence emissivity coefficient of the fluorescence reference sample and a spectral power distribution of the first illumination light, a fluorescence spectral emissivity coefficient Bf2($\lambda$) by a second illumination light is calculated by using equations (3) and (4) from the bispectral fluorescence emissivity coefficient and a spectral power distribution of the second illumination light, a fluorescence spectral emissivity coefficient Bf($\lambda$) by a standard illumination light is calculated by using equations (3) and (4) from the bispectral fluorescence emissivity coefficient and the spectral power distribution of the standard illumination light, and a weighting coefficient W($\lambda$) is set such that a linear combination W($\lambda$)·Bf1($\lambda$)+(1−W($\lambda$))·Bf2($\lambda$) of Bf1($\lambda$) and Bf2($\lambda$) equals to Bf($\lambda$).

As described above, since there is a problem with the conventional approximate measuring method, improvement of the approximate measuring method is required.

CITATION LIST

Patent Literature

Patent Literature 1: JP 08-313349 A
Patent Literature 2: JP 2006-292510 A

SUMMARY OF INVENTION

Technical Problem

An object of the present invention is to provide a method for measuring spectral radiation characteristics of a fluorescence whitened sample capable of improving an approximate measuring method, and a device for measuring spectral radiation characteristics of the fluorescence whitened sample.

Solution to Problem

In order to realize the object described above, a method for measuring spectral radiation characteristics of a fluorescence whitened sample reflecting an aspect of the present invention is a method for measuring spectral radiation characteristics of a fluorescence whitened sample illuminated with a standard illumination light Id, the method provided with:

obtaining an approximation B'f(Id,$\lambda$) of a fluorescence spectral emissivity coefficient Bf(Id,$\lambda$) by the standard illumination light Id at following first to third steps from spectral power distributions R(Ik,$\lambda$) of sample radiation lights generated when the fluorescence whitened sample is sequentially illuminated with a plurality of excitation lights Ik (k=1 to n) having different spectral power distributions and a spectral power distribution Id($\lambda$) of the standard illumination light Id. First step: Spectral power distributions Rf(Ik,$\lambda$) of fluorescence are obtained from the spectral power distributions R(Ik,λ) by respective excitation lights Ik. Second step: The spectral power distributions Rf(Ik,λ) of fluorescence by the respective excitation lights Ik are linearly combined with a given weighting coefficient Wk, and an approximation R'f(Id,λ) of a spectral power distribution Rf(Id,λ) of fluorescence by the standard illumination light Id is obtained by following equation (6).

[Math. 6]

$$R'_f(I_d, \lambda) = \sum_k W_k \cdot R_f(I_k, \lambda) \quad \text{Equation (6)}$$

Third step: The approximation B'f(Id,λ) is obtained by following equation (7) from the approximation R'f(Id,λ) and the spectral power distribution Id(λ) of the standard illumination light Id.

[Math. 7]

$$B'_f(I_d, \lambda) = \frac{R'_f(I_d, \lambda)}{I_d(\lambda)} \quad \text{Equation (7)}$$

Advantages and features provided by one or a plurality embodiments of the invention are fully understood from the detailed description provided below and the accompanying drawings. These detailed descriptions and the accompanying drawings are provided by way of example only and are not intended as a definition of the limitations of the invention.

BRIEF DESCRIPTION OF DRAWINGS

FIG. 3 is a graph illustrating spectral powers of various illumination lights used in an embodiment.

FIG. 4 is a view illustrating fluorescence whitened paper divided into four types.

FIG. 5 is a graph illustrating the spectral power of the illumination light approximating D50 in an overlapping range.

FIG. 7 is an illustrative diagram explaining a configuration of a device for measuring a fluorescence whitened sample according to a first embodiment.

DESCRIPTION OF EMBODIMENTS

Figure 1:
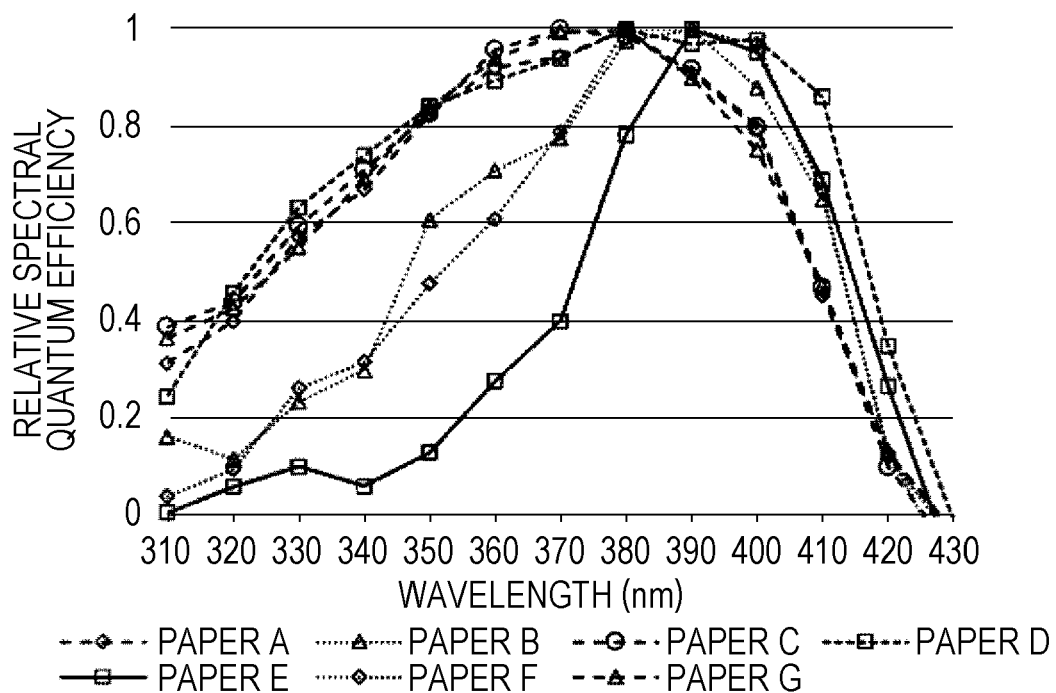
FIG. 1 is a graph illustrating a relationship between a wavelength and a relative spectral quantum efficiency regarding seven types of common fluorescence whitened paper.

One or a plurality of embodiments of the present invention is hereinafter described with reference to the drawings. However, the scope of the invention is not limited to the disclosed embodiment.

An outline of the embodiment is described. In the embodiment, an approximation B't(Id,λ) of a total spectral emissivity coefficient Bt(Id,λ) by a standard illumination light Id is obtained using the following equation. Note that the "approximation" may be reworded as an "approximation value".

$$B't(Id,\lambda)=B'r(\lambda)+B'f(Id,\lambda)$$

B'r(λ) is an approximation of a spectral reflectivity coefficient Br(λ). B'f(Id,λ) is an approximation of a fluorescence spectral emissivity coefficient Bf(Id,λ) by the standard illumination light Id. As described next, the approximations B'r(λ) and B'f(Id,λ) are obtained without using a specific bispectral fluorescence emissivity coefficient F(μ,λ). As a result, the approximation B't(Id,λ) may be obtained without using the specific bispectral fluorescence emissivity coefficient F(μ,λ). According to the embodiment, it is possible to improve accuracy of the approximations B'r(λ) and B'f(Id,λ), thereby improving accuracy of the approximation B't(Id,λ).

The approximation B'f(Id,λ) is obtained by using following equation (7). Id(λ) represents a spectral power distribution of the standard illumination light Id. R'f(Id,λ) represents an approximation of a spectral power distribution Rf(Id,λ) of fluorescence by the standard illumination light Id. This approximation R'f(Id,λ) is obtained by using following equation (6). Rf(Ik,λ) represents spectral power distributions of fluorescence by a plurality of illumination lights (excitation lights) Ik (k=1 to n). Wk represents a weighting coefficient.

In this manner, in order to obtain the approximation B'f(Id,λ), not the specific bispectral fluorescence emissivity coefficient but the standard illumination light Id is used. Since no fluorescence is generated from a wavelength range outside an excitation range, the wavelength range outside the excitation range is not necessary to obtain the approximation B'f(Id,λ). Therefore, it is sufficient that a spectral component of the excitation range (300 to 420 nm) coincides with a spectral component of 300 to 420 nm of the standard illumination light. The inventor focuses on the fact that such a light source may be realized by a small number of monochromatic LEDs (a small number of illumination lights Ik described above).

The approximation B'r(λ) is obtained by using following equation (16). Ivis(λ) represents a spectral power distribution of measuring range illumination light Ivis (visible range illumination light). R(Ivis,λ) represents a spectral power distribution of a sample radiation light (=sample reflected light+fluorescence) by the measuring range illumination light Ivis. Rr(Ivis,λ) represents a spectral power distribution of the sample reflected light by the measuring range illumination light Ivis. Rf(Ivis,λ) represents a spectral power distribution of fluorescence by the measuring range illumination light Ivis. As expressed in a latter half of equation (16), Rf(Ivis,λ) is subtracted from R(Ivis,λ). Therefore, according to this approximation B'r(λ), an effect of fluorescence may be removed, so that it is possible to meet requirements of the paper manufacturing industry. Hereinafter, the embodiment is described in detail.

<Measurement Principle>

The embodiment uses an approximate measuring method. The embodiment is based on equation (2) in which the approximation B'f(Id,λ) of the fluorescence spectral emissivity coefficient Bf(Id,λ) by the standard illumination light Id and the approximation B'r(λ) of the spectral reflectivity coefficient Br(λ) by the standard illumination light Id are obtained, and the sum of the approximation B'f(Id,λ) and the approximation B'r(λ) is obtained. In the embodiment, this sum is the approximation B't(Id,λ) of the total spectral emissivity coefficient Bt(Id,λ) by the standard illumination light Id.

[A] Approximate Measurement of Fluorescence Spectral Emissivity Coefficient Bf(Id,λ)

In order to obtain the fluorescence spectral emissivity coefficient Bf(Id,λ) by the standard illumination light Id for fluorescence whitened paper having various bispectral fluorescence emissivity coefficients, the illumination light having the spectral power distribution approximating the spectral power distribution Id(λ) of the standard illumination light Id at least in the excitation range (300 to 420 nm) is required. However, it is difficult to practically realize this. Therefore, as expressed by equation (6), it is considered to approximate the spectral power distribution Rf(Id,λ) of fluorescence by the standard illumination light Id by using a spectral power distribution of synthetic fluorescence obtained by linearly combining the spectral power distributions Rf(Ik,λ) of fluorescence by a plurality of illumination lights (excitation lights) Ik (k=1 to n) having different spectral power distributions in the excitation wavelength range by an appropriate weighting coefficient Wk (right side in equation (6) (left side in equation (6)).

[Math. 8]

$$R'_f(I_d, \lambda) = \sum_k W_k \cdot R_f(I_k, \lambda) \quad \text{Equation (6)}$$

FIG. 1 is a graph illustrating a relationship between a wavelength and a relative spectral quantum efficiency regarding seven types of common fluorescence whitened paper. As illustrated in FIG. 1, there is similarity among the relative spectral quantum efficiencies of the commonly used fluorescence whitened paper and they may be classified into a plurality of appropriately set types. In a case where the illumination light (excitation light) Ik suitable for the set type is selected and the weighting coefficient Wk is optimized, the right side of equation (6) (synthetic fluorescence spectral power distribution) becomes an excellent approximation (R'f(Id,λ)) of the spectral power distribution Rf(Id,λ) of fluorescence by the standard illumination light Id as for the fluorescence whitened paper which may be classified into the type. From the approximation R'f(Id,λ) and the known spectral power distribution Id(λ) of the standard illumination light Id, the approximation B'f(Id,λ) of the fluorescence spectral emissivity coefficient Bf(Id,λ) by the standard illumination light Id is obtained by equation (7). As described above, the approximation B'f(Id,λ) is obtained without using the specific bispectral fluorescence emissivity coefficient F(μ,λ).

[Math. 9]

$$B'_f(I_d, \lambda) = \frac{R'_f(I_d, \lambda)}{I_d(\lambda)} \quad \text{Equation (7)}$$

Commercially available illumination light of the monochromatic LED may be used as the excitation light Ik. Sufficient accuracy may be obtained even with a small number of monochromatic illumination lights Ik by using the excitation light Ik of an appropriate wavelength.

The radiation light (reflected light+fluorescence) is generated from the fluorescence whitened paper irradiated with the illumination light. In a case where a wavelength range of the reflected light and a wavelength range of the fluorescence have an overlapping range, not equation (6) but following equation (11) is used. This is hereinafter described in detail.

FIG. 3 is a graph illustrating a relationship between wavelengths of various types of LEDs and the spectral power. A method of obtaining the approximation R'f(Id,λ) is described taking a case where two monochromatic illumination lights I1 and I2 having the LED with a central wavelength of 360 nm (UV360 in FIG. 3) and the LED with a central wavelength of 405 nm (V405 in FIG. 3) as light sources are used as an example for the sake of simplicity.

Figure 2:
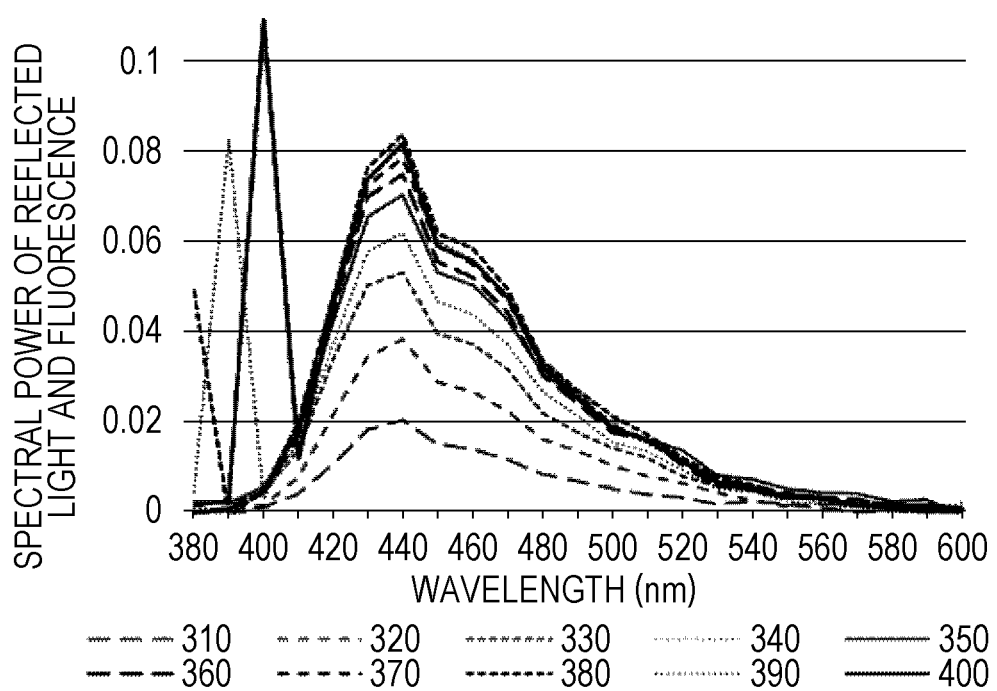
FIG. 2 is a graph illustrating spectral powers when the seven types of common fluorescence whitened paper are irradiated with monochromatic light.

FIG. 2 is a graph illustrating the spectral powers when the seven types of common fluorescence whitened paper are irradiated with the monochromatic light. The spectral power include the spectral power of the reflected light and the spectral power of the fluorescence. As illustrated in FIG. 2, a fluorescence range of the common fluorescence whitened paper is 390 to 600 nm, but the excitation light having the power within the fluorescence range has the overlapping range where the fluorescence and the reflected light much stronger than the same coexist. The measuring range is set to a visible range of 400 to 700 nm. A spectral power distribution R(I1,λ) of 400 to 700 nm provides a spectral power distribution Rf(I1,λ) of fluorescence in the sample radiation light by the monochromatic illumination light I1 having the central wavelength of 360 nm and no overlapping range in the fluorescence range (390 to 600 nm) (the spectral power distribution Rf(Ik,λ) of fluorescence is obtained from the spectral power distribution R(Ik,λ) by each excitation light Ik: a spectral power distribution Rf(Ik1,λ) of fluorescence by a first type of excitation light Ik1 is provided by a spectral power distribution R(Ik1,λ) of a sample radiation light by the first type of excitation light Ik1). That is, in a case of the monochromatic illumination light I1, since there is no wavelength range of the reflected light in the wavelength range of the fluorescence, Rf(Ik,λ) included in equation (6) may be obtained (measured). On the other hand, in the sample radiation light by the monochromatic illumination light I2 having a central wavelength of 405 nm and the overlapping range (390 to 430 nm) in the fluorescence range (390 to 600 nm), a spectral power distribution Rf(I2,λ) of fluorescence is provided outside the overlapping range (430 to 700 nm), but a spectral power distribution Rf(I2,λ) of fluorescence is not provided within the overlapping range (400 to 430 nm) due to an effect of the reflected light. That is, in a case of the monochromatic illumination light I2, Rf(Ik,λ) included in equation (6) cannot be obtained within the overlapping range. Therefore, in a case of the monochromatic illumination light I2, an approximation R'f(I2,λ) is obtained. When this is described in detail, as illustrated in FIG. 2, the relative spectral power distribution of fluorescence does not depend on the excitation wavelength and is almost constant, so that it is possible to replace the spectral power distribution in the overlapping range of fluorescence by the monochromatic illumination light I2 with K·I1(λ) by using a spectral power distribution Rf(I1,λr1) of fluorescence by the monochromatic illumination light I1. However, a coefficient K for adjusting the power is provided by equation (8) by a ratio between the spectral power distributions Rf(I1,λr1) and Rf(I2,λr1) of fluorescence by the monochromatic illumination lights I1 and I2 at one or more reference wavelength λr1 outside the overlapping range (for example, 440 nm). The coefficient K may be reworded as a ratio between the spectral power distributions R(I1,λr1) and R(I2,λr1) of the sample radiation lights by the monochromatic illumination lights I1 and I2 at the reference wavelength λr1.

[Math. 10]

$$K = \frac{R_f(I_2, \lambda_{r1})}{R_f(I_1, \lambda_{r1})} = \frac{R(I_2, \lambda_{r1})}{R(I_1, \lambda_{r1})}$$ Equation (8)

Furthermore, the fluorescence wavelength λ introduces a correction coefficient C(λ) reflecting that this is always longer than the excitation wavelength μ, and provides by equation (9) the approximation R'f(I2,λ) of the spectral power distribution Rf(I2,λ) of fluorescence by the monochromatic illumination light I2. Equation (9a) expresses a case within the overlapping range, and equation (9b) expresses a case outside the overlapping range. Outside the overlapping range, as described above, the spectral power distribution Rf(I2,λ) of fluorescence by the monochromatic illumination light I2 is provided, so that this is used as the approximation R'f(I2,λ). Note that, in equation (9a), Rf(I1,λ) may be reworded as R(I1,λ), and in equation (9b), Rf(I2,λ) may be reworded as R(I2,λ).

[Math. 11]

$$R'_f(I_2, \lambda) = R_f(I_1, \lambda) \cdot K \cdot C(\lambda) \quad 400 \leq \lambda < 430 \text{ nm} \quad \text{Equation (9a)}$$
$$= R_f(I_2, \lambda) \quad \lambda \geq 430 \text{ nm} \quad \text{Equation (9b)}$$

Herein, the correction coefficient C(λ) is provided by equation (10). μ represents the above-described excitation wavelength. In a case of the correction coefficient C(λ), λ represents the fluorescence wavelength.

[Math. 12]

$$C(\lambda) = 1 - \frac{\sum_{\mu=\lambda}^{\infty} I_2(\mu)}{\sum_{\mu=m}^{\infty} I_2(\mu)} \quad 400 \leq \lambda < 430 \text{ nm}$$ Equation (10)

The approximation R'f(Id,λ) of the spectral power distribution Rf(Id,λ) of fluorescence by the standard illumination light Id is provided by equation (11) by using the spectral power distribution of Rf(I1,λ) of fluorescence by the monochromatic illumination light I1 and the approximation R'f(I2,λ) of the spectral power distribution Rf(I2,λ) of fluorescence by the monochromatic illumination light I2.

[Math. 13]

$$R'_f(I_d, \lambda) = W_1 \cdot R_f(I_1, \lambda) + W_2 \cdot R'_f(I_2, \lambda)$$ Equation (11)

[B] Setting of Weighting Coefficient Wk

There are setting methods 1 to 3 as setting methods of the weighting coefficient Wk. This is hereinafter described in detail. In a case where a sufficient number of monochromatic excitation lights Ik are distributed in the excitation range, the weighting coefficient Wk is set such that a spectral power distribution I'd(λ) of a synthetic excitation light I'd provided by equation (12) approximates the spectral power distribution Id(λ) of the standard illumination light Id (setting method 1).

[Math. 14]

$$I'_d(\lambda) = \sum_k W_k \cdot I_k(\lambda)$$ Equation (12)

The setting method 2 is described. In a case where a sufficient number of monochromatic excitation lights Ik are not distributed in the excitation range, it is not possible to approximate the spectral power distribution Id(λ) of the standard illumination light Id. In this case, the weighting coefficient Wk is optimized such that the spectral power distribution of synthetic fluorescence expressed by the right side of equation (6) for the common fluorescence whitened paper approximates the fluorescence spectral power distribution Rf(Id,λ) by the standard illumination light Id.

For example, the relative spectral quantum efficiencies of representative fluorescence whitened paper (paper A, paper B, paper C, paper D, paper E, paper F, and paper G) illustrated in FIG. 1 may be classified into four types illustrated in FIG. 4. Bispectral fluorescence emissivity coefficients FT(μ,λ) of the whitened paper (paper D, paper E, paper F, and paper G) representing respective types T (T=1 to 4) are obtained (the bispectral fluorescence emissivity coefficients $FT(\mu,\lambda)$ of the fluorescence whitened samples to be measured are classified into a plurality of types, and a plurality of different bispectral fluorescence emissivity coefficients is a plurality of types of bispectral fluorescence emissivity coefficients). Then, W1 and W2 are set such that the spectral power distribution of synthetic fluorescence $(=R'f,T(Id,\lambda))$ obtained by linearly combining the spectral power distribution $Rf,T(I1,\lambda)$ of fluorescence by the monochromatic illumination light I1 and the spectral power distribution $Rf,T(I2,\lambda)$ of fluorescence by the monochromatic illumination light I2, $Rf,T(I1,\lambda)$ and $Rf,T(I2,\lambda)$ of each type obtained by equation (4) by equation (36) approximates the spectral power distribution $Rf,T(Id,\lambda)$ of fluorescence by the standard illumination light Id (setting method 2).

[Math. 15]

$$R'_f(I_d,\lambda) = W_1 \cdot R_f(I_1,\lambda) + W_2 \cdot R_f(I_2,\lambda) \quad \text{Equation (36)}$$

A generalized description of the setting method 2 is as follows. Spectral power distributions $Rf,T(Ik,\lambda)$ of fluorescence by a plurality of excitation lights Ik and a spectral power distribution $Rf,T(Id,\lambda)$ of fluorescence by the standard illumination light Id are obtained by following equations (25) and (26) from a plurality of different bispectral fluorescence emissivity coefficients $FT(\mu, \lambda)$(T=1 to N), the spectral power distributions $Ik(\lambda)$ of a plurality of excitation lights Ik, and the spectral power distribution $Id(\lambda)$ of the standard illumination light Id. In a case of the bispectral fluorescence emissivity coefficient $FT(\mu, \lambda)$, $\mu$ represents the excitation wavelength and $\lambda$ represents the fluorescence wavelength.

[Math. 16]

$$R_{f,T}(I_k,\lambda) = \int I_k(\mu) F_T(\mu,\lambda) d\mu \quad \text{Equation (25)}$$

[Math. 17]

$$R_{f,T}(I_d,\lambda) = \int I_d(\mu) F_T(\mu,\lambda) d\mu \quad \text{Equation (26)}$$

Then, the weighting coefficient Wk is set such that the spectral power distribution $R'f,T(Id,\lambda)$ of synthetic fluorescence obtained by linearly combining the spectral power distributions $Rf,T(Ik,\lambda)$ of fluorescence by a plurality of excitation lights Ik by following equation (27) approximates the spectral power distribution $Rf,T(Id,\lambda)$ of fluorescence by the standard illumination light Id for all of a plurality of bispectral fluorescence emissivity coefficients $FT(\mu,\lambda)$.

[Math. 18]

$$R'_{f,T}(I_d, \lambda) = \sum_k W_k \cdot R_{f,T}(I_k, \lambda) \quad \text{Equation (27)}$$

The setting method 3 is described. As described above, the relative spectral power distribution of fluorescence does not depend on the excitation wavelength and is almost constant, so that it is possible to replace $Rf,T(I1,\lambda)$, $Rf,T(I2,\lambda)$, and $Rf,T(Id,\lambda)$ described above with fluorescence powers $Rf,T(I1,\lambda r2)$, $Rf,T(I2,\lambda r2)$, and $Rf,T(Id,\lambda,r2)$ at one or more wavelengths $\lambda r2$ (for example, wavelength of 440 nm close to a peak not affected by reflection of the excitation light). Therefore, the weighting coefficients W1 and W2 such that the sum of squares $dRf \times dRf$ of a difference between $R'f,T(Id,\lambda r2)$ and $Rf,T(Id,\lambda r2)$ of each type provided by equation (13) becomes the minimum may be obtained by a least square method (setting method 3). $Rf,T(I1,\lambda r2)$, $Rf,T(I2,\lambda r2)$, and $Rf,T(Id,\lambda r2)$ are obtained by equations (14) and (15) from a spectral quantum efficiency $FT(\mu,\lambda r2)$ for the fluorescence at the wavelength $\lambda r2$ of each type obtained in advance and spectral power distributions $I1(\mu)$, $I2(\mu)$, and $Id(\mu)$ of each illumination light. Note that the spectral quantum efficiency $FT(\mu,\lambda r2)$ for the fluorescence at the wavelength $\lambda r2$ of each type is as follows. The spectral quantum efficiencies $FT(\mu,\lambda r2)$ for the fluorescence at the reference wavelength $\lambda r2$ of the fluorescence whitened sample to be measured are classified into a plurality of types, and a plurality of different spectral quantum efficiencies is a plurality of types of spectral quantum efficiencies.

[Math. 19]

$$dR_f^2 = \sum_T (R'_{f,T}(I_d, \lambda_{r2}) - R_{f,T}(I_d, \lambda_{r2}))^2 \quad (T = 1 \sim 4) \quad \text{Equation (13)}$$

[Math. 20]

$$R_{f,T}(I_k, \lambda_{t2}) = \int I_k(\mu) F_T(\mu, \lambda_{t2}) d\mu \quad (k = 1, 2) \quad \text{Equation (14)}$$

[Math. 21]

$$R_{f,T}(I_d, \lambda_{t2}) = \int I_d(\mu) F_T(\mu, \lambda_{t2}) d\mu \quad \text{Equation (15)}$$

Although one set of weighting coefficients Wk for one standard illumination light Id is set above, it is possible to set M sets of weighting coefficients Wk,m for M standard illumination lights Id,m (m=1 to M) selected from a plurality of standard illumination lights Id (for example, A, C, D50, and D65), apply the weighting coefficients Wk,m to the same spectral power distribution $Rf(Ik,\lambda)$ of fluorescence, obtain the approximation $R'f(Id,\lambda)$ by using equation (6), and obtain an approximation $B'f(Id,m,\lambda)$ of a fluorescence spectral emissivity coefficient $Bf(Id,m,\lambda)$ by the selected standard illumination light Id,m and an approximation $B't(Id,m,\lambda)$ of a total spectral emissivity coefficient $Bt(Id,m,\lambda)$ by the selected standard illumination light Id,m.

[C] Approximate Measurement of Spectral Reflectivity Coefficient $Br(\lambda)$

As expressed in a first half of equation (16), the approximation $B'r(\lambda)$ of the spectral reflectivity coefficient $Br(\lambda)$ is obtained by dividing the spectral power distribution $Rr(Ivis,\lambda)$ of the sample reflected light by the measuring range illumination light Ivis by the spectral power distribution $Ivis(\lambda)$ of the measuring range illumination light Ivis. On the other hand, as illustrated in FIG. 1, the excitation range of the common fluorescence whitened paper extends to 430 nm, and most of fluorescence whitened paper has a high quantum efficiency at 390 to 410 nm. For this reason, the spectral power distribution $R(Ivis,\lambda)$ of the sample radiation light generated when the fluorescence whitened paper is illuminated with the visible range (measuring range) illumination light Ivis includes not only the spectral power distribution $Rr(Ivis,\lambda)$ of the sample reflected light but also the spectral power distribution $Rf(Ivis,\lambda)$ of fluorescence excited by a component of 430 nm or shorter of the visible range (measuring range) illumination light Ivis. Therefore, as expressed in a latter half of equation (16), the spectral power distribution Rr(Ivis,λ) of the sample reflected light by the visible range (measuring range) illumination light Ivis is obtained by subtracting the spectral power distribution Rf(Ivis,λ) of fluorescence by the visible range (measuring range) illumination light Ivis from the spectral power distribution R(Ivis,λ) of the sample radiation light by the visible range (measuring range) illumination light Ivis, and this is divided by the spectral power distribution Ivis(λ) of the visible range (measuring range) illumination light Ivis, thereby obtaining the approximation B'r(λ) of the spectral reflectivity coefficient Br(λ).

[Math. 22]

$$B'_r(\lambda) = \frac{R_r(I_{VIS}, \lambda)}{I_{VIS}(\lambda)} = \frac{R(I_{VIS}, \lambda) - R_f(I_{VIS}, \lambda)}{I_{VIS}(\lambda)} \quad \text{Equation (16)}$$

In order to estimate Rf(Ivis,λ), the visible range (measuring range) illumination light Ivis covering the visible range of 400 nm to 700 nm is synthesized by an illumination light Ivis1 not shorter than 430 nm not exciting fluorescence and an illumination light Ivis2 of 400 nm to 430 nm exciting the fluorescence. Specifically, the former is a blue-excited white LED Iwb (Wb in FIG. 3) having the spectral power distribution illustrated in FIG. 3, and the latter is the monochromatic illumination light I2 having a central wavelength of 405 nm (V405 in FIG. 3), and the spectral power distribution Ivis(λ) of the visible range (measuring range) illumination light Ivis is provided by equation (17).

[Math. 23]

$$I_{VIS}(\lambda) = I_{Wb}(\lambda) + I_2(\lambda) \quad \text{Equation (17)}$$

In this case, the spectral power distribution R(Ivis,λ) of the sample radiation light by the visible range (measuring range) illumination light Ivis is provided by equation (18).

[Math. 24]

$$R(I_{VIS}, \lambda) = R(I_{Wb}, \lambda) + R(I_2, \lambda) \quad \text{Equation (18)}$$

The spectral power distribution Rf(Ivis,λ) of fluorescence by the visible range (measuring range) illumination light Ivis is approximated by R'f(I2,λ) provided by equation (9a). That is, Rf(Ivis,λ) is used as R'f(I2,λ) (since Ivis=I2 in 400 nm to 430 nm, it is possible to approximate). The same, equation (17), and equation (18) are substituted into equation (16) to obtain the approximation B'r(λ) of the spectral reflectivity coefficient Br(λ).

[D] Calculation of Approximation B't(Id,λ) of Total Spectral Emissivity Coefficient Bt(Id,λ)

As in equation (2), the approximation B't(Id,λ) of the total spectral emissivity coefficient Bt(Id,λ) by the standard illumination light Id is obtained. Specifically, the approximation R'f(Id,λ) is obtained by using equation (11). The approximation B'f(Id,λ) is obtained by using the approximation R'f(Id,λ) and equation (7). The approximation B'r(λ) is obtained by using equation (16). The sum of the approximation B'f(Id,λ) and the approximation B'r(λ) is obtained. This is the approximation B't(Id,λ).

[E] Different Method of Measuring Total Spectral Reflectivity Coefficient Bt(Id,λ)

A different method is a method of obtaining an approximation B''t(Id,λ) of the total spectral emissivity coefficient Bt(Id,λ) by the standard illumination light Id without using the spectral reflectivity coefficient and the correction coefficient C(λ) expressed by equation (10) regarding the overlapping range. As expressed by following equations (20a) and (20b), the approximation B''t(Id,λ) is obtained separately in the overlapping range (400≤λ<430 nm) and outside the overlapping range (λ≥430 nm). This is hereinafter described in detail.

As described in the measurement principle [A], an overlapping range component of the spectral power distribution Rf(I2,λ) of fluorescence by the monochromatic illumination light I2 (excitation light) in the overlapping range where the fluorescence range and the excitation range overlap is not obtained from the spectral power distribution R(I2,λ) of the radiation light including the fluorescence by the excitation light and the reflected light. Therefore, the approximation R'f(I2,λ) of the spectral power distribution Rf(I2,λ) of fluorescence by the monochromatic illumination light I2 (excitation light) is obtained by equations (8), (9a), and (10). In equation (9a), the correction coefficient C(λ) reflecting that the fluorescence wavelength λ is always longer than the excitation wavelength μ is also introduced. This different method is proposed to avoid such troublesome handling of the overlapping range. FIG. 5 is a graph illustrating a relationship between a wavelength and spectral power for a D50 light source and a Id2 light source used in the different method. The Id2 light source is a light source which emits an overlapping range illumination light Id2 having a spectral power distribution approximating the standard illumination light Id (herein, D50 light source) in the overlapping range (400 to 430 nm). Since the overlapping range (400 to 430 nm) is a relatively narrow wavelength range, it is possible to realize the Id2 light source only by combining a small number of LEDs. In the different method, a total spectral reflectivity coefficient Bt(Id2,λ) of the overlapping range by the overlapping range illumination light Id2 is obtained (equation (19)) not as the sum of the fluorescence spectral emissivity coefficient and the spectral reflectivity coefficient but directly from a spectral power distribution R(Id2,λ) of the sample radiation light by the overlapping range illumination light Id2.

[Math. 25]

$$B_t(I_{d2}, \lambda) = \frac{R(I_{d2}, \lambda)}{I_{d2}(\lambda)} \quad 400 \text{ nm} \leq \lambda \leq 430 \text{ nm} \quad \text{Equation (19)}$$

Figure 6:
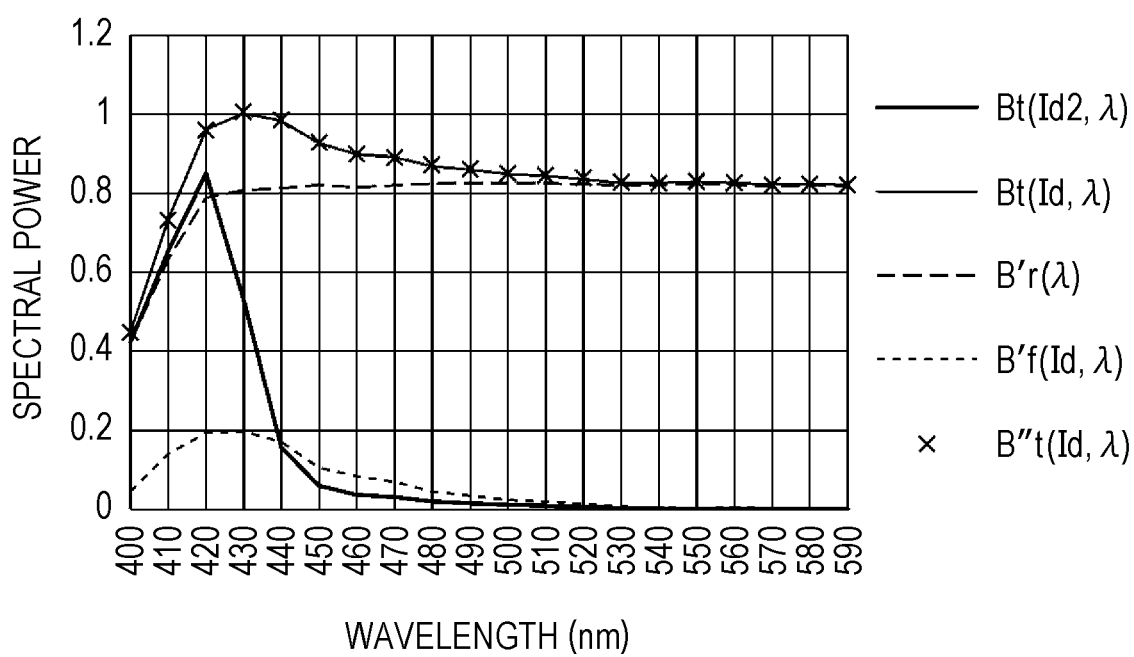
FIG. 6 is a graph illustrating a relationship between a wavelength and a spectral power for various coefficients used in a different method.

FIG. 6 is a graph illustrating a relationship between a wavelength and spectral power for various coefficients used in the different method. Only a fluorescence spectral emissivity coefficient Bf(Id2,λ) by the overlapping range component Id2 of the standard illumination light Id is included in Bt(Id2,λ) of the overlapping range by equation (19). Therefore, as expressed in a first half of equation (20a), it is necessary to add a fluorescence spectral emissivity coefficient Bf(Id1,λ) by an excitation component (component of <400 nm) Id1 other than the overlapping range component Id2 of the standard illumination light Id. The sum of Bf(Id1,λ) and Bt(Id2,λ) expressed by equation (19) is the approximation B''t(Id,λ) of the total spectral emissivity coefficient Bt(Id,λ) by the standard illumination light Id as expressed in the first half of equation (20a). Bf(Id1,λ) described above has a relative shape the same as that of the approximation B'f(Id,λ) obtained by equations (6) and (7). Therefore, as expressed in a latter half of equation (20a), it is possible to approximate by B'f(Id1,λ) with A as a power coefficient.

Outside the overlapping range, the approximation B″t(Id, λ) of the total spectral emissivity coefficient Bt(Id,λ) by the standard illumination light Id is provided by equation (20b) on the basis of equation (2). That is, the approximation B″t(Id,λ) is the sum of the approximation B′f(Id,λ) obtained by equations (6) and (7) and the spectral reflectivity coefficient Br(λ) obtained by equation (20c). A method of obtaining Br(λ) is as follows. Herein, since only outside the overlapping range is the target, the measuring range illumination light Ivis may be replaced with the illumination light Ivis1 (measuring range illumination light not including the excitation range). Since the illumination light Ivis1 does not excite the fluorescence, it is obtained by equation (20c) as R(Ivis1,λ)=Rr(Ivis1,λ) and Rf(Ivis1,λ)=0. Also, since a target of equations (20a) and (20b) is fluorescence of a long wavelength by the excitation light, the correction coefficient C(λ) included in equation (9a) becomes unnecessary.

[Math. 26]

$$B''_t(I_d, \lambda) = B_t(I_{d2}, \lambda) + B_t(I_{d1}, \lambda) = B_i(I_{d2}, \lambda) + A \cdot B'_f(I_d, \lambda) \quad 400 \text{ nm} \leq \lambda < 430 \text{ nm} \quad \text{Equation (20a)}$$

$$= B'_f(I_d, \lambda) + B_r(\lambda) \quad \lambda \geq 430 \text{ nm} \quad \text{Equation (20b)}$$

$$B_t(\lambda) = \frac{R_t(I_{VIS}, \lambda)}{I_{VIS}(\lambda)} \quad \lambda \geq 430 \text{ nm} \quad \text{Equation (20c)}$$

The power coefficient A is provided by equation (21). λr3 represents one or more reference wavelengths (for example, 460 nm) not affected by the reflected light of the illumination light Ivis 2 (measuring range illumination light including the excitation range, illumination light of 400 to 430 nm). Bt(Id2,λr3) represents a total spectral emissivity coefficient by the overlapping range illumination light Id2. B′f(Id,λr3) represents an approximation of the fluorescence spectral emissivity coefficient by the standard illumination light Id.

[Math. 27]

$$A = 1 - \frac{B_t(I_{d2}, \lambda_{r3})}{B'_f(I_d, \lambda_{r3})} \quad \text{Equation (21)}$$

The measurement principle is heretofore described.

First Embodiment

FIG. 7 is an illustrative diagram explaining a configuration of a device for measuring fluorescence whitened sample according to a first embodiment. The first embodiment uses two monochromatic excitation lights Ik, and is provided with an integrating sphere 4 having an inner wall with high diffusion and high reflectivity. From apertures 1a, 2a, and 3a formed in the integrating sphere 4, a radiation light 1b of a blue-excited white LED 1 (illumination light Iwb radiated from the blue-excited white LED), a radiation light 2b of a ultraviolet LED 2 with a central wavelength of 360 nm (monochromatic illumination light I1), and a radiation light 3b of a violet LED 3 with a central wavelength of 405 nm (monochromatic illumination light I2) are incident, respectively. The white LED 1, the ultraviolet LED 2, and the violet LED 3 are sequentially lighted up by driving signals 1e, 2e, and 3e output by a control arithmetic device 10 (control arithmetic unit) via driving circuits 1d, 2d, and 3d, respectively. The radiation lights 1b, 2b, and 3b are multiply diffused and reflected by the inner wall of the integrating sphere 4 to be a diffused illumination light 4a, and the diffused illumination light 4a diffusely illuminates a sample 5 (fluorescence whitened sample) placed in a sample aperture 5a. Out of the radiation light radiated from the sample 5 by the illumination, a normal component 5b is converged to be incident on an incident end 7a of a sample optical fiber 7 by an objective lens 6 through a measuring aperture 5c of the integrating sphere 4, and is guided to a sample optical slit 7b of a dual channel spectrometer 9 (sample radiation light spectroscopic unit) by the sample optical fiber 7. This illumination light receiving system conforms to d:0° SCE geometry required by ISO 5631-1, 2, 3 regarding paper measurement. In contrast, a part of the illumination light in the integrating sphere 4 is incident on a reference optical fiber 8 through a reference aperture 8a and is guided to a reference optical slit 8b of the dual channel spectrometer 9 by the reference optical fiber 8. The dual channel spectrometer 9 outputs spectral power distribution data 9a of the incident sample radiation light and reference light to the control arithmetic device 10. The control arithmetic device 10 controls and lights up the white LED 1, the ultraviolet LED 2, and the purple LED 3, and controls the dual channel spectrometer 9 to measure the spectral power distributions of the sample radiation light and the reference light, obtains an approximation of a fluorescence spectral emissivity coefficient of the sample 5 and an approximation of a spectral reflectivity coefficient by using the spectral power distribution data which is transmitted and given data, calculates an approximation of a total spectral emissivity coefficient therefrom, and outputs the approximation of the fluorescence spectral reflectivity coefficient, the approximation of the spectral reflectivity coefficient, and the approximation of the total spectral emissivity coefficient as output data 10a.

The control arithmetic device 10 (control arithmetic unit) is realized by, for example, hardware processors such as a central processing unit (CPU), a random access memory (RAM), a read only memory (ROM), and a hard disk drive (HDD), and a program, data and the like for executing a function of the control arithmetic device 10. Some or all of functions of the control arithmetic device 10 may also be realized by processing by a digital signal processor (DSP) in place of or in addition to processing by the CPU. Also, some or all of the functions of the control arithmetic device 10 may be realized by processing by a dedicated hardware circuit in place of or in addition to processing by software.

Figure 8A:
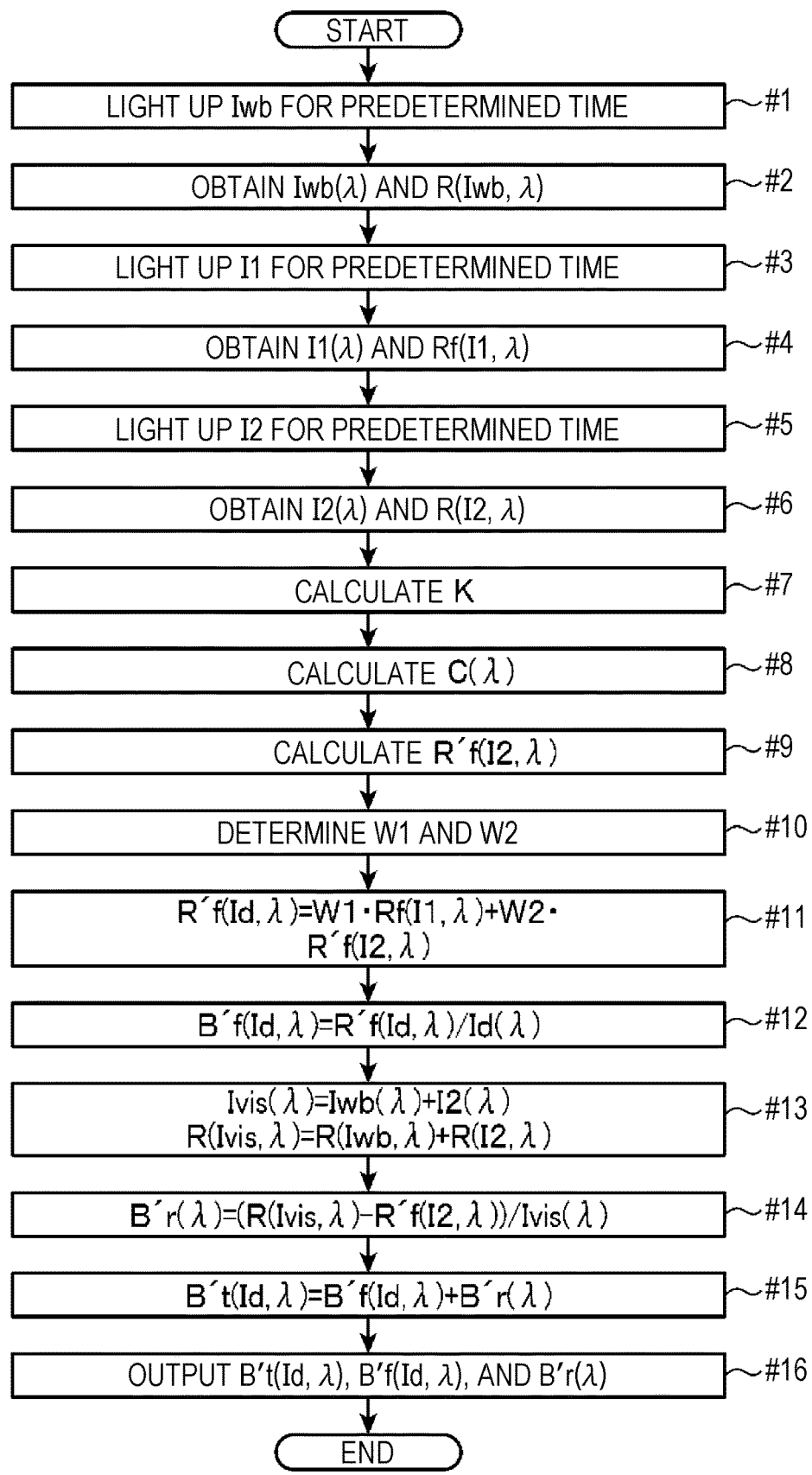
FIG. 8A is a flowchart illustrating a method for measuring spectral radiation characteristics of the fluorescence whitened sample according to the first embodiment.

FIG. 8A is a flowchart illustrating a method for measuring spectral radiation characteristics of the fluorescence whitened sample according to the first embodiment. In order to obtain an approximation B′f(Id,λ) of a fluorescence spectral emissivity coefficient Bf(Id,λ) by the standard illumination light Id, the standard illumination light Id is required. Only an excitation range contributes to generation of fluorescence, so that it is sufficient if a spectral component of the excitation range (300 to 420 nm) of the standard illumination light Id may be realized. In the first embodiment, the spectral component of the excitation range of the standard illumination light Id is realized by a light source (ultraviolet LED 2) of the monochromatic illumination light I1 having the central wavelength of 360 nm and a light source (purple LED 3) of the monochromatic illumination light I2 having the central wavelength of 405 nm. In order to obtain an approximation $B'r(\lambda)$ of a spectral reflectivity coefficient $Br(\lambda)$, a light source in a visible range (400 to 700 nm) is required. In the first embodiment, the light source is realized by a light source (white LED 1) of the illumination light Iwb and a light source (violet LED 3) of the monochromatic illumination light I2 having the central wavelength of 405 nm. Hereinafter, a method for measuring the spectral radiation characteristics is described with reference to FIGS. 7 and 8A.

The control arithmetic device 10 lights up the light source (white LED 1) of the illumination light Iwb for a predetermined time (#1).

The control arithmetic device 10 obtains a spectral power distribution $Iwb(\lambda)$ of the illumination light Iwb and a spectral power distribution $R(Iwb,\lambda)$ of the sample radiation light by the illumination light Iwb from the dual channel spectrometer 9 (#2).

The control arithmetic device 10 lights up the light source (ultraviolet LED 2) of the monochromatic illumination light I1 having the central wavelength of 360 nm for a predetermined time (#3).

The control arithmetic device 10 obtains a spectral power distribution $I1(\lambda)$ of the monochromatic illumination light I1 and a spectral power distribution $R(I1,\lambda)(=Rf(I1,\lambda))$ of the sample radiation light by the monochromatic illumination light I1 (#4).

The control arithmetic device 10 lights up the light source (violet LED 3) of the monochromatic illumination light I2 having the central wavelength of 405 nm for a predetermined time (#5).

The control arithmetic device 10 obtains a spectral power distribution $I2(\lambda)$ of the monochromatic illumination light I2 and a spectral power distribution $R(I2,\lambda)$ of the sample radiation light by the monochromatic illumination light I2 (#6).

The control arithmetic device 10 obtains a power coefficient K by $R(I1,\lambda)$ obtained at #4, $R(I2,\lambda)$ obtained at #6, and equation (8) (#7).

The control arithmetic device 10 obtains a correction coefficient $C(\lambda)$ by equation (10) (#8).

The control arithmetic device 10 obtains an approximation $R'f(I2,\lambda)$ of a spectral power distribution $Rf(I2,\lambda)$ of fluorescence by the monochromatic illumination light I2 by K, $C(\lambda)$, and equations (9a) and (9b) (#9).

The control arithmetic device 10 executes a weighting coefficient optimizing subroutine by using the spectral power distribution $Id(\lambda)$ of the monochromatic illumination light I1, the spectral power distribution $I2(\lambda)$ of the monochromatic illumination light I2, and a spectral quantum efficiency $FT(\mu,440)$ of each type stored in advance, thereby obtaining weighting coefficients W1 and W2 (#10).

The control arithmetic device 10 uses the obtained weighting coefficients W1 and W2 to obtain an approximation $R'f(Id,\lambda)$ of a spectral power distribution $Rf(Id,\lambda)$ of fluorescence by the standard illumination light Id by equation (11) (#11).

The control arithmetic device 10 obtains an approximation $B'f(Id,\lambda)$ of a fluorescence spectral emissivity coefficient $Bf(Id,\lambda)$ by the standard illumination light Id by the approximation $R'f(Id,\lambda)$, a spectral power distribution $Id(\lambda)$ of the standard illumination light Id, and equation (7) (#12).

The control arithmetic device 10 synthesizes a spectral power distribution $Ivis(\lambda)$ of a measuring range illumination light Ivis and a spectral power distribution $R(Ivis,\lambda)$ of the sample radiation light by the measuring range illumination light Ivis by the spectral power distribution $Iwb(\lambda)$ of the illumination light Iwb, the spectral power distribution $I2(\lambda)$ of the monochromatic illumination light I2, the spectral power distribution $R(Iwb,\lambda)$ of the sample radiation light by the illumination light Iwb, the spectral power distribution $R(I2,\lambda)$ of the sample radiation light by the monochromatic illumination light I2, equation (17), and equation (18) (#13).

The control arithmetic device 10 obtains an approximation $B'r(\lambda)$ of a spectral reflectivity coefficient $Br(\lambda)$ by using $Ivis(\lambda)$ and $R(Ivis,\lambda)$ obtained at #13, the approximation $R'f(I2,\lambda)$ obtained at #9, and equation (16) (#14). A reason that the approximation $R'f(I2,\lambda)$ obtained at #9 may be used as the spectral power distribution $Rf(Ivis,\lambda)$ of fluorescence by the measuring range illumination light Ivis included in equation (16) is described. Since the illumination light Iwb has no wavelength component in the excitation range, fluorescence is generated by the monochromatic illumination light I2. Therefore, with regard to fluorescence, the measuring range illumination light Ivis may be regarded as the monochromatic illumination light I2. Therefore, approximation $R'f(I2,\lambda)$=approximation $R'f(Ivis,\lambda) \approx Rf(Ivis,\lambda)$ is satisfied.

The control arithmetic device 10 adds the approximation $B'r(\lambda)$ obtained at #14 to the approximation $B'f(Id,\lambda)$ obtained at #12 to obtain an approximation $B't(Id,\lambda)$ of a total spectral emissivity coefficient $Bt(Id,\lambda)$ by the standard illumination light Id (#15).

The control arithmetic device 10 outputs the approximations $B'f(Id,\lambda)$, $B'r(\lambda)$, and $B't(Id,\lambda)$ (#16).

Figure 8B:
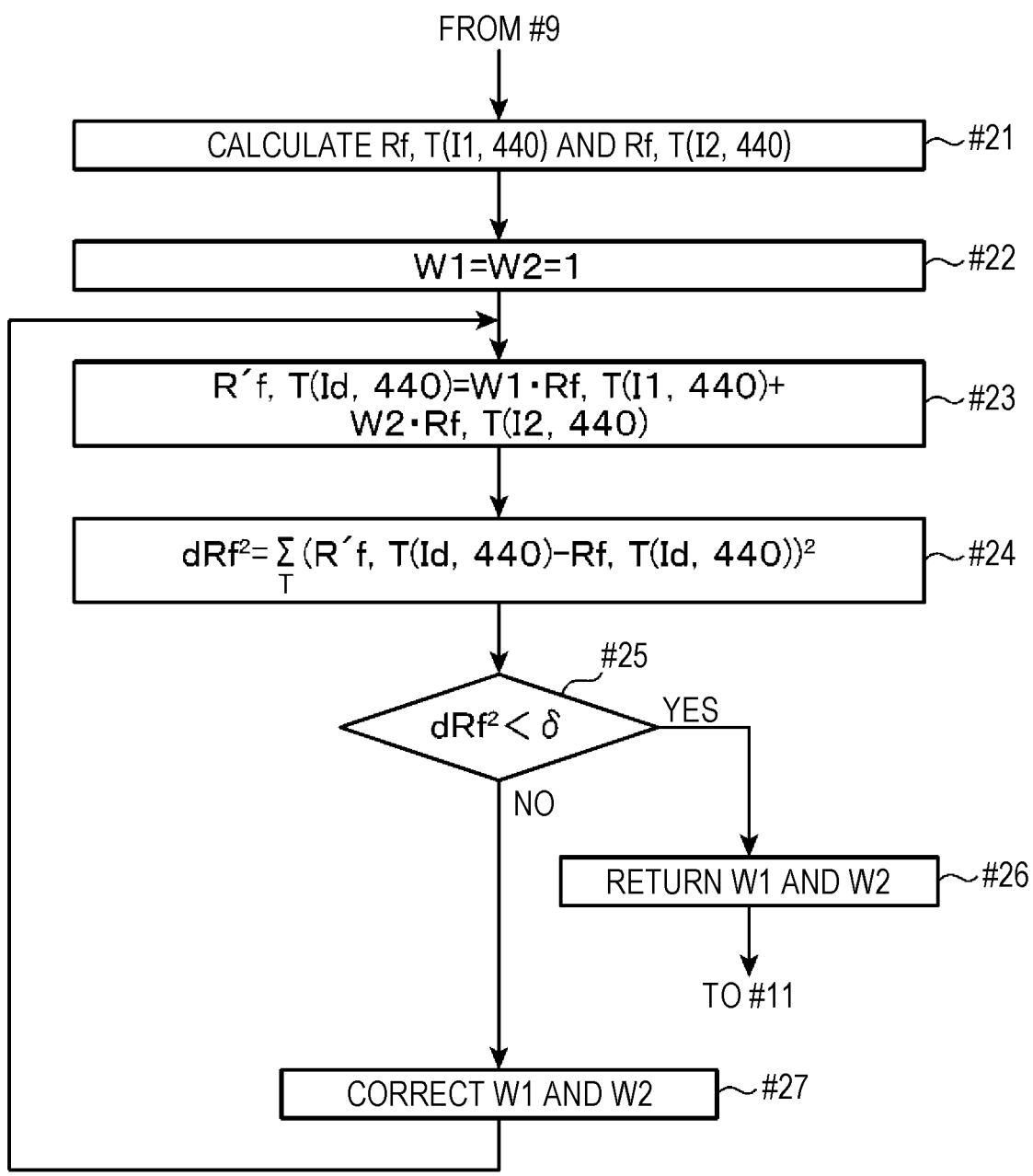
FIG. 8B is a flowchart illustrating a weighting coefficient optimizing subroutine at #10.

Hereinafter, a flow of the weighting coefficient optimizing subroutine at #10 is described. FIG. 8B is a flowchart illustrating this subroutine. $\lambda r2$ is set to 440 nm. With reference to FIGS. 7 and 8B, in the control arithmetic device 10, the spectral quantum efficiency $FT(\mu,440)$ for 440 nm fluorescence of each type T (T=1 to 4) obtained in advance, and fluorescence power $Rf,T(Id,440)$ at 440 nm by the standard illumination light Id obtained by $FT(\mu,440)$, $Id(\mu)$, and equation (15) are stored.

The control arithmetic device 10 obtains fluorescence powers $Rf,T(I1,440)$ and $Rf,T(I2,440)$ by the monochromatic illumination lights I1 and I2 of each type T by using $FT(\mu,440)$, the spectral power distribution $I1(\lambda)$ of the monochromatic illumination light I1, the spectral power distribution $I2(\lambda)$ of the monochromatic illumination light I2, and equation (14) (#21).

The control arithmetic device 10 sets the weighting coefficients W1 and W2 to an initial value 1 (#22).

The control arithmetic device 10 linearly combines $Rf,T(I1,440)$ and $Rf,T(I2,440)$ obtained at #21 by the weighting coefficients W1 and W2 by equation (11) to obtain a synthetic power $R'f,T(Id,440)$ (#23).

The control arithmetic device 10 obtains the sum of squares $dRf \times dRf$ of a difference between $R'f,T(Id,440)$ of each type T and $Rf,T(Id,440)$ described above stored in advance by equation (13) (#24).

The control arithmetic device 10 determines whether the sum of squares $dRf \times dRf$ is smaller than a given threshold $\delta$ (#25).

In a case where the sum of squares $dRf \times dRf$ is smaller than the given threshold $\delta$ (Yes), the control arithmetic device 10 returns the weighting coefficient W1 and W2 used at #23 to a main routine (#26).

In a case where the sum of squares dRf×dRf is equal to or larger than the given threshold δ (No), the control arithmetic device 10 returns to #23 to correct the weighting coefficient W1 and W2 (#27).

In the flow illustrated in FIGS. 8A and 8B, the weighting coefficients W1 and W2 are reset in the weighting coefficient optimizing subroutine at #10 on the basis of the spectral power distribution B(λ) of the monochromatic illumination light I1 and the spectral power distribution I2(λ) of the monochromatic illumination light I2 obtained for each measurement in consideration of the fact that temperature dependency of the spectral power distribution of the LED radiation light is large (that is, a weighting coefficient Wk for setting the powers of a plurality of excitation lights Ik (k=1 to n) is obtained on the basis of a spectral power distribution Ik(μ) of an excitation light Ik obtained in the most recent measurement). However, in a case where the spectral power distributions I1(λ) and I2(λ) are stable or change is ignorable, the weighting coefficient set and stored at the time of manufacture or before measurement may be used.

A spectral power distribution of a monochromatic LED depends on element temperature, and a forward voltage of the LED driven at constant current also depends on the element temperature. Therefore, the control arithmetic device 10 may obtain in advance correlation characteristics between the forward voltage at the time of constant current driving and the spectral power distribution and estimate the spectral power distribution of the monochromatic LED from the forward voltage detected at the time of measurement under the same driving condition. The driving circuit 1d (driving unit) drives the white LED 1 (monochromatic LED) at the constant current. The driving circuit 2d (driving unit) drives the ultraviolet LED 2 (monochromatic LED) at the constant current. The driving circuit 3d (driving unit) drives the violet LED 3 (monochromatic LED) at the constant current.

Furthermore, the control arithmetic device 10 may obtain in advance a table illustrating a relationship between the forward voltage (that is, the element temperature) of the monochromatic LED and the weighting coefficients W1 and W2 in the spectral power distributions I1(λ) and I2(λ) at the forward voltage and obtain the weighting coefficient at the forward voltage at the time of measurement by interpolation or the like. The driving circuit 1d is provided with a voltage measuring circuit which measures the forward voltage of the white LED 1 (monochromatic LED). The driving circuit 2d is provided with a voltage measuring circuit which measures the forward voltage of the ultraviolet LED 2 (monochromatic LED). The driving circuit 3d is provided with a voltage measuring circuit which measures the forward voltage of the violet LED 3 (monochromatic LED). Each of these voltage measuring circuits (forward voltage measuring units) is formed of an operational amplifier and an AD converter. A noninverting input terminal of the operational amplifier is connected to a cathode of the monochromatic LED. An inverting input terminal and an output terminal of the operational amplifier are connected. The output terminal of the operational amplifier is connected to an input terminal of the AD converter.

Also, at #7 to #9, regarding the spectral power distribution R'f(I2,λ) of fluorescence by the monochromatic illumination light I2, a case of a component in an overlapping range is obtained by equation (9a), and a case of a component outside the overlapping range is obtained by equation (9b). However, also a case of the component outside the overlapping range may be obtained by equation (9a). In this case, the correction coefficient C(λ)=1 represented by equation (10) is satisfied.

Second Embodiment

Figure 9:
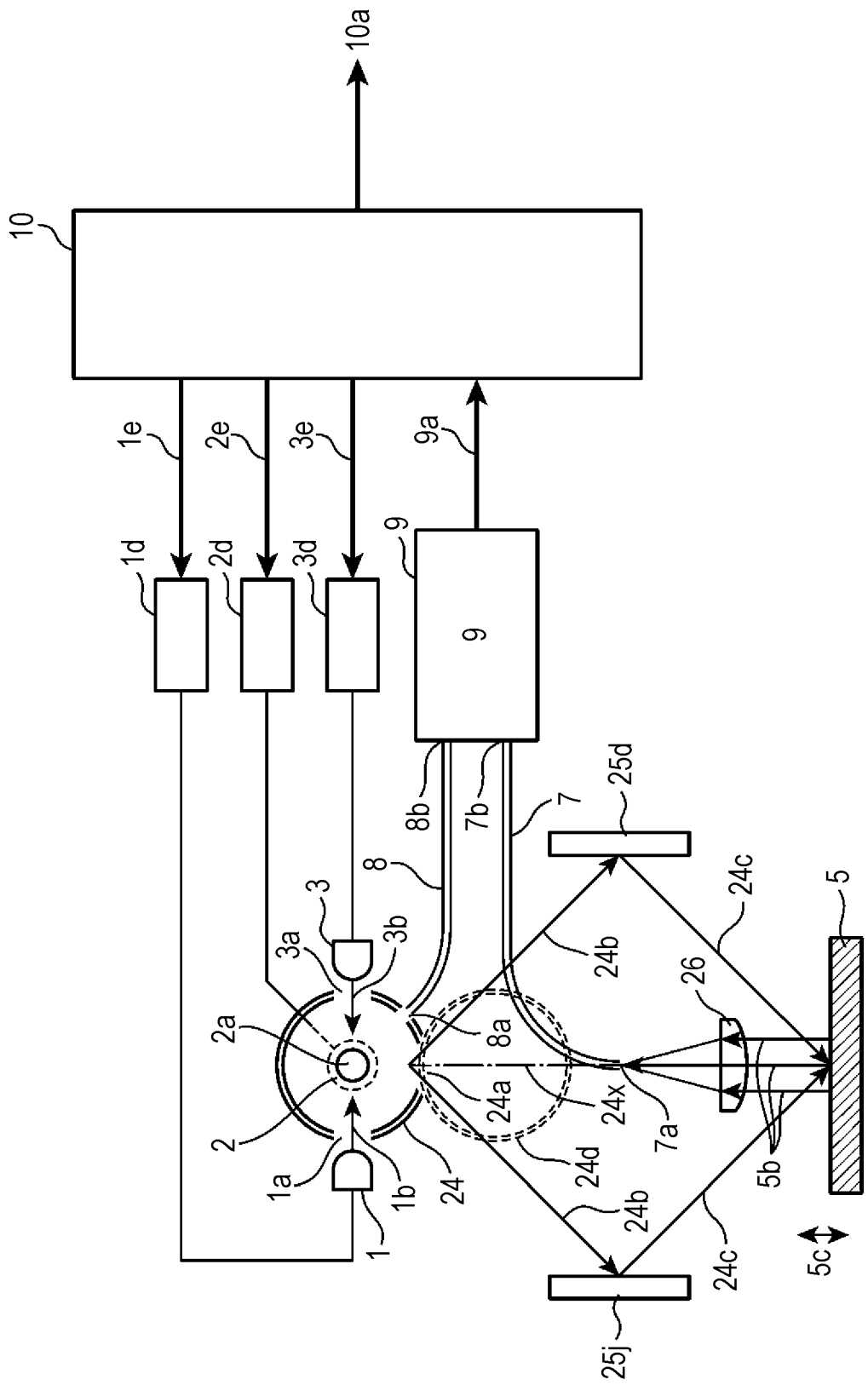
FIG. 9 is an illustrative diagram explaining a configuration of a device for measuring a fluorescence whitened sample according to a second embodiment.
Figure 10:
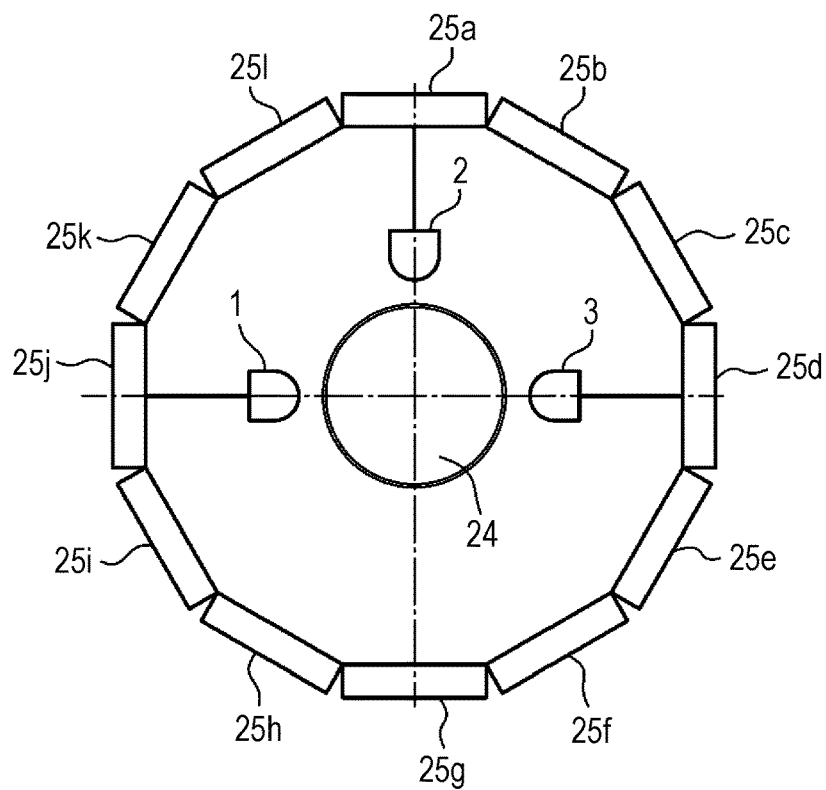
FIG. 10 is a plan view of an illumination optical system provided in the device for measuring the fluorescence whitened sample according to the second embodiment.

FIG. 9 is an illustrative diagram explaining a configuration of a device for measuring a fluorescence whitened sample according to a second embodiment. FIG. 10 is a plan view of an illumination optical system provided in the device for measuring the fluorescence whitened sample according to the second embodiment. The second embodiment is different from the first embodiment only in an illumination light receiving optical system. An illumination system of the second embodiment is provided with a small integrating sphere 24, and as in the first embodiment, a radiation light 1b of a blue-excited white LED 1 (Iwb), a radiation light 2b of a ultraviolet LED 2 with a central wavelength of 360 nm (I1), and a radiation light 3b of a violet LED 3 with a central wavelength of 405 nm (I2) are incident from apertures 1a, 2a, and 3a. The radiation lights 1b, 2b, and 3b are diffused and radiated from a radiating aperture 24a after multiple diffusion/reflection on an inner wall of the small integrating sphere 24. An optical axis 24x of the illumination light receiving optical system coincides with a normal to a radiating aperture plane passing through the center of the radiating aperture plane. A radiation light component 24b near 45° from the optical axis 24x is reflected by 12 plane mirrors 25a to 25l (FIG. 10) arranged in axial symmetry with respect to the optical axis 24x. Reflected light fluxes illuminate a sample 5 from 12 directions as illumination light 24c centered at 45° from the optical axis 24x. A normal component 5b of a sample radiation light by this illumination is converged and incident on an incident end 7a of a sample optical fiber 7 by an objective lens 26, and is guided to a sample optical slit 7b of a dual channel spectrometer 9 by the sample optical fiber 7. This illumination light receiving system conforms to a 45° c: 0° geometry required by ISO 13655 regarding measurement of a printed matter. On the other hand, a part of the illumination light in the small integrating sphere 24 is incident on a reference optical fiber 8 through a reference aperture 8a and is guided to a reference optical slit 8b of the dual channel spectrometer 9 by the reference optical fiber 8. The dual channel spectrometer 9 outputs spectral power distribution data 9a of the incident sample light and reference light to a control arithmetic device 10. Control of the white LED 1, the ultraviolet LED 2, and the violet LED 3 and processing of the spectral power distribution data are performed by a flow in FIGS. 8A and 8B.

Since the radiation light from the radiating aperture 24a of the small integrating sphere 24 has light distribution 24d of a COS characteristic, a change in illuminance on a sample surface is suppressed even when variation 5c occurs in a distance between the illumination optical system and the sample 5 (sample surface) as disclosed in Literatures (U.S. Pat. No. 7,365,843, JP 2010-281808 A).

Third Embodiment

Figure 11:
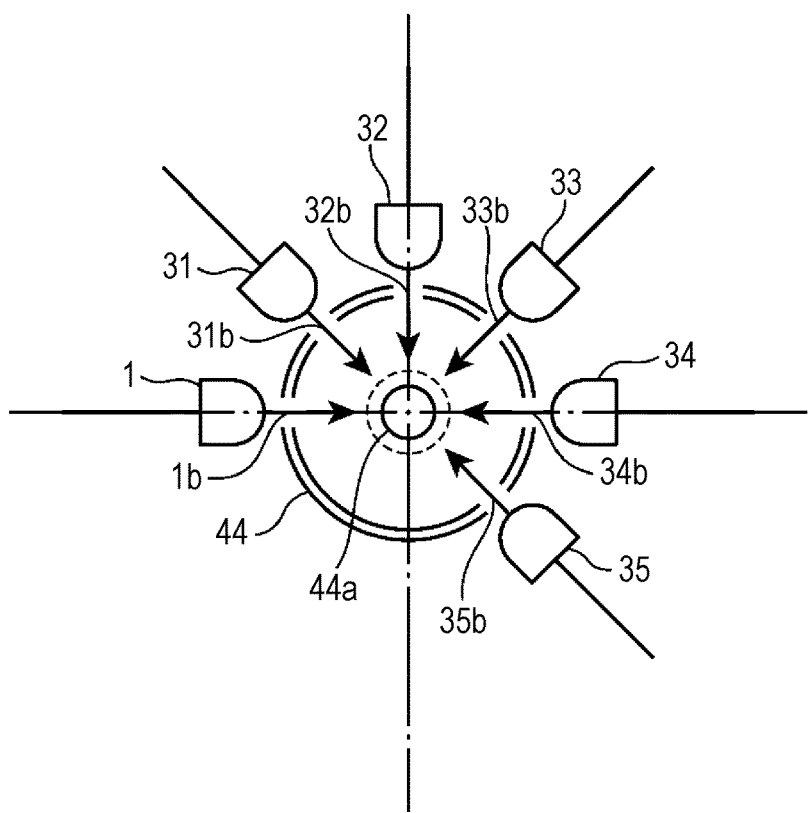
FIG. 11 is a plan view illustrating a radiation light incident on a small integrating sphere in a third embodiment.
Figure 12:
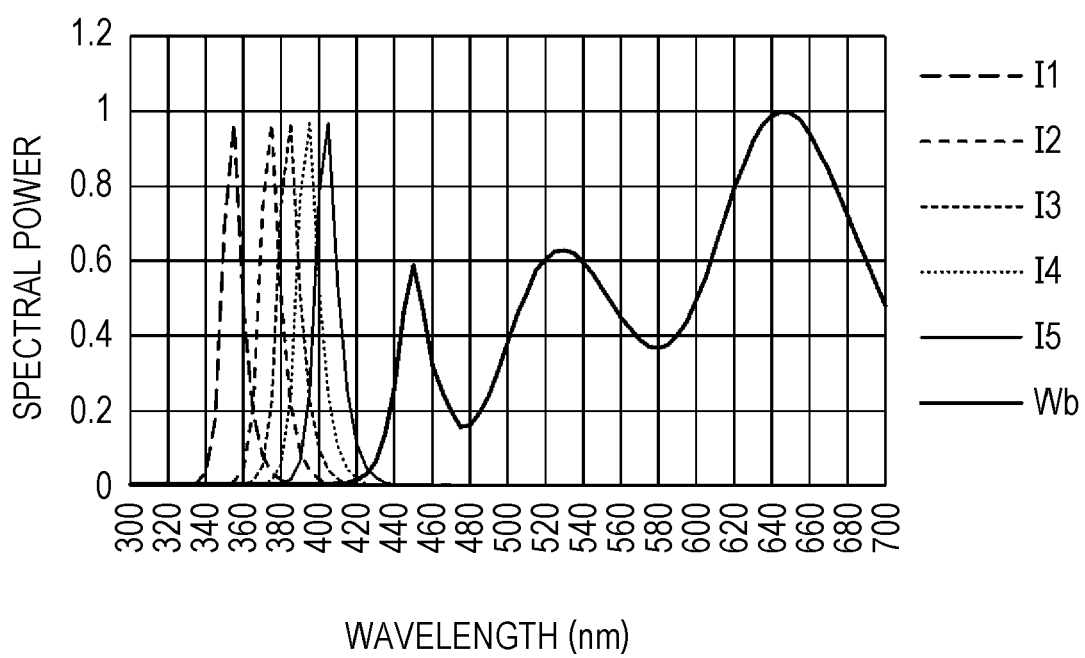
FIG. 12 is a graph illustrating spectral powers of radiation lights (Iwb, I1, I2, I3, I4, and I5) used in the third embodiment.

FIG. 11 is a plan view illustrating a radiation light incident on a small integrating sphere in a third embodiment. A method for measuring a fluorescence whitened sample according to the third embodiment basically has the same configuration as that of the second embodiment, but as illustrated in FIG. 11, a radiation light 1b (Iwb) of a blue-excited white LED 1, a radiation light 31b (I1) of an LED 31 having a central wavelength of 355 nm, a radiation light 32*b* (I2) of an LED 32 of 375 nm, a radiation light 33*b* (I3) of an LED 33 of 385 nm, a radiation light 34*b* (I4) of an LED 34 of 395 nm, and a radiation light 35*b* (I5) of an LED 35 of 405 nm are incident on a small integrating sphere 44 from corresponding apertures. FIG. 12 is a graph illustrating spectral powers of the radiation lights (Iwb, I1, I2, I3, I4, and I5) used in the third embodiment. In the setting method 3, weighting coefficients W1 to W5 of five excitation lights I1 to I5 cannot be optimized on the basis of four types of spectral quantum efficiencies Ff,T($\mu$,440) in FIG. 4. Therefore, in the third embodiment, the weighting coefficients W2 to W5 of the excitation lights I2 to I5 are set by the setting method 1. Furthermore, in order to reflect excitation outside the excitation lights I1 to I5 (~355 nm and 405 nm~), the weighting coefficient W1 of the excitation light I1 and the weighting coefficient W5 of the excitation light I5 are set by the setting method 3 (weighting coefficient W5 is reset).

Figure 13:
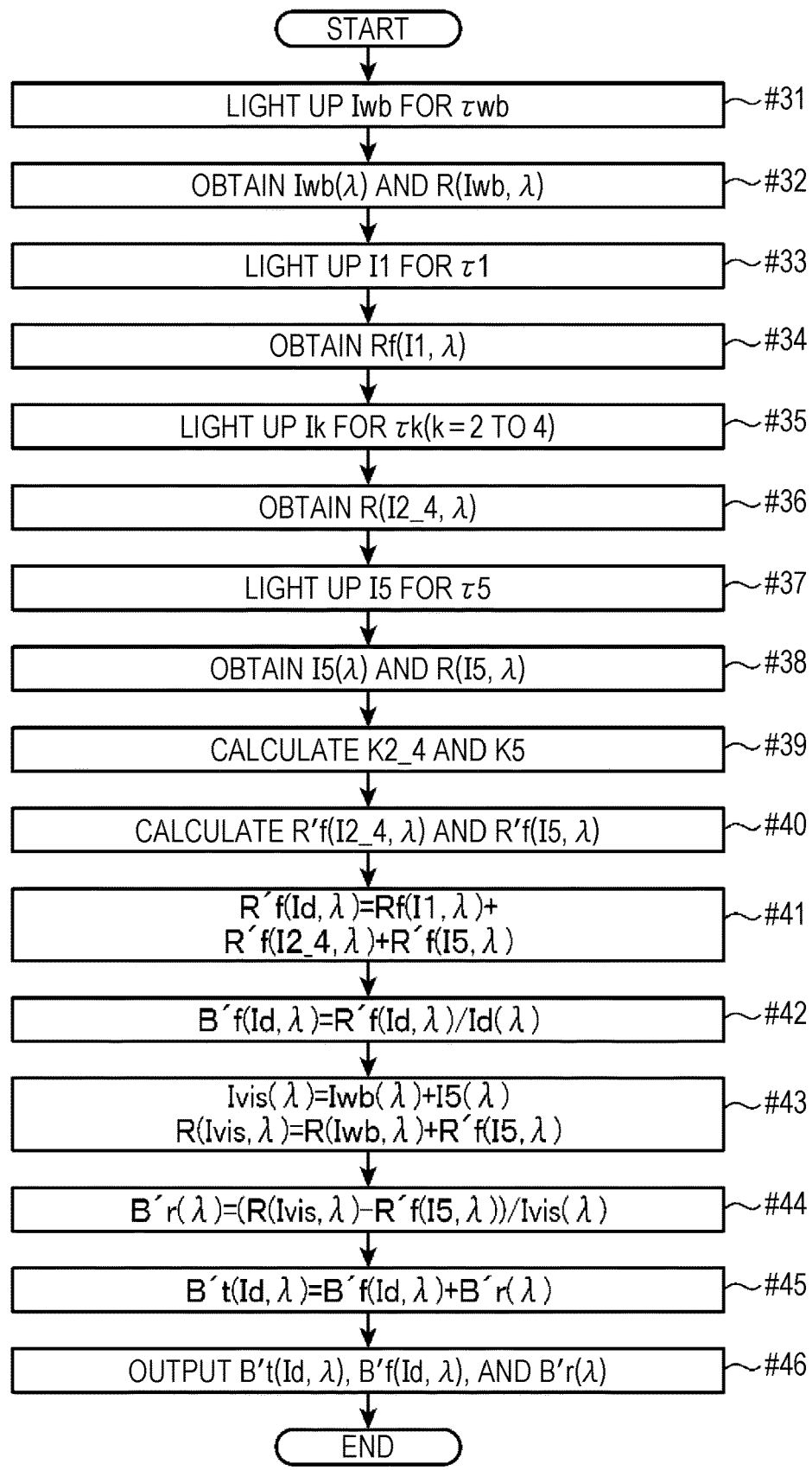
FIG. 13 is a flowchart illustrating a method for measuring spectral radiation characteristics of the fluorescence whitened sample according to the third embodiment.

FIG. 13 is a flowchart illustrating a method for measuring spectral radiation characteristics of the fluorescence whitened sample according to the third embodiment. Weighting of linear combination performed by arithmetic operation in a flow in FIG. 8A and FIG. 8B is performed by controlling a lighting time $\tau k$ of the LED such that the power of the excitation lights Ik (k=1 to n) is proportional to a weighting coefficient Wk in this flow. The lighting time $\tau k$ of the excitation light Ik and a lighting time $\tau wb$ of an illumination light Iwb based on the weighting coefficient Wk are provided in advance, and four types of illumination lights of Iwb, I1, I2_4 (=I2+I3+I4), and I5 are used. Since a correction coefficient C2_4($\lambda$) of I2_4 and a correction coefficient C5($\lambda$) of I5 depend only on spectral power distributions thereof, they may be obtained at this stage according to equation (10).

A control arithmetic device 10 lights up a light source (white LED 1) of the illumination light Iwb for the time $\tau wb$ (#31).

The control arithmetic device 10 obtains a spectral power distribution Iwb($\lambda$) of the illumination light Iwb and a spectral power distribution R(Iwb,$\lambda$) of a sample radiation light by the illumination light Iwb from a dual channel spectrometer 9 (#32).

The control arithmetic device 10 lights up a light source (LED) of the excitation light I1 having a central wavelength of 355 nm for a time $\tau 1$ (#33).

The control arithmetic device 10 obtains a spectral power distribution R(I1,$\lambda$) (=Rf(I1,$\lambda$)) of a sample radiation light by the excitation light I1 (#34).

The control arithmetic device 10 lights up a light source (LED) of the excitation light I2 having a central wavelength of 375 nm for a time $\tau 2$, a light source (LED) of the excitation light I3 having a central wavelength of 385 nm for a time $\tau 3$, and a light source (LED) of the excitation light I4 having a central wavelength of 395 nm for a time $\tau 4$ (#35).

The control arithmetic device 10 obtains a spectral power distribution R(I2_4,$\lambda$) of a sample radiation light by the excitation lights I2+I3+I4 (#36).

The control arithmetic device 10 lights up a light source (LED) of the excitation light I5 having a central wavelength of 405 nm for a time $\tau 5$ (#37).

The control arithmetic device 10 obtains a spectral power distribution I5($\lambda$) of the excitation light I5 and a spectral power distribution R(I5,$\lambda$) of a sample radiation light by the excitation light I5 (#38).

The control arithmetic device 10 obtains power coefficients K2_4 and K5 by equation (8) (#39).

The control arithmetic device 10 obtains an approximation R'f(I2_4,$\lambda$) of a spectral power distribution Rf(I2_4,$\lambda$) of fluorescence by the excitation light I2_4, and an approximation R'f(I5,$\lambda$) of a spectral power distribution Rf(I5,$\lambda$) of fluorescence by the excitation light I5 by K2_4, K5, C2_4($\lambda$), C5($\lambda$), equation (9a), and equation (9b) (#40).

The control arithmetic device 10 adds R(I1,$\lambda$) and the approximations R'(I2_4,$\lambda$) and R'f(I5,$\lambda$) to obtain an approximation R'f(Id,$\lambda$) of a spectral power distribution Rf(Id,$\lambda$) of fluorescence by a standard illumination light Id (#41).

The control arithmetic device 10 obtains an approximation B'f(Id,$\lambda$) of a fluorescence spectral emissivity coefficient Bf(Id,$\lambda$) by the standard illumination light Id by the approximation R'f (Id,$\lambda$), the spectral power distribution Id($\lambda$) of the standard illumination light Id, and equation (7) (#42).

The control arithmetic device 10 synthesizes a spectral power distribution Ivis($\lambda$) of a measuring range illumination light Ivis and a spectral power distribution R(Ivis,$\lambda$) of a sample radiation light by the measuring range illumination light Ivis by the spectral power distribution Iwb($\lambda$) of the illumination light Iwb, the spectral power distribution I5($\lambda$) of the excitation light I5, the spectral power distribution R(Iwb,$\lambda$) of the sample radiation light by the illumination light Iwb, the spectral power distribution R(I5,$\lambda$) of the sample radiation light by the excitation light I5, equation (17), and equation (18) (#43).

The control arithmetic device 10 obtains an approximation B'r($\lambda$) of a spectral reflectivity coefficient Br($\lambda$) by using Ivis,($\lambda$) and R(Ivis,$\lambda$) obtained at #43, the approximation R'f(I5,$\lambda$)(=R'f(Ivis,$\lambda$)) obtained at #40, and equation (16) (#44).

The control arithmetic device 10 adds the approximation B'r($\lambda$) obtained at #44 to the approximation B'f(Id,$\lambda$) obtained at #42 to obtain the approximation B't(Id,$\lambda$) of the total spectral emissivity coefficient Bt(Id,$\lambda$) by the standard illumination light Id (#45).

The control arithmetic device 10 outputs the approximation B'f(Id,$\lambda$), the approximation B'r($\lambda$), and the approximation B't(Id,$\lambda$) (#46).

Although the power is provided by the lighting time $\tau k$ above, it is also possible to provide this by a driving current amount ik of the LED. Although $\tau k$ and ik must be known before measurement, in a case of continuous measurement as in scan measurement, the control arithmetic device 10 may obtain a spectral power distribution Ik($\lambda$) for each measurement, and obtain $\tau k$ and ik for next measurement. In a case of simultaneous lighting, individual spectral power distribution Ik($\lambda$) cannot be measured, but it is possible to obtain the individual spectral power distribution Ik($\lambda$) in a case where the LED is driven at constant current and the spectral power distribution is estimated from forward voltage as described above.

Fourth Embodiment

Figure 14:
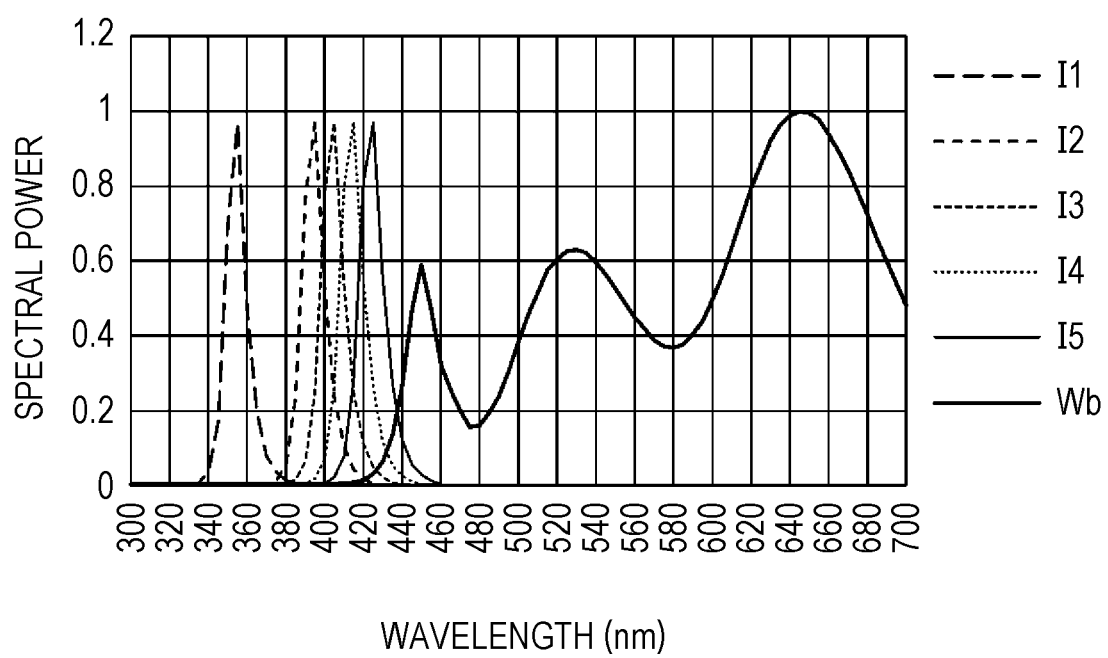
FIG. 14 is a graph illustrating spectral power of each of radiation lights (Iwb, I1, I2, I3, I4, and I5) used in a fourth embodiment.

A fourth embodiment uses a different method to calculate an approximation B't(Id,$\lambda$) of a total spectral reflectivity coefficient. The fourth embodiment is basically the same in configuration as the third embodiment, but a central wavelength of a monochromatic light incident on a small integrating sphere 44 of an illumination light receiving system illustrated in FIG. 11 is different. That is, although a radiation light 1*b* (Iwb) of a blue-excited white LED 1 and a radiation light 31*b* (I1) of an LED 31 having a central wavelength of 355 nm do not change, central wavelengths of a radiation light 32b (I2) of an LED 32, a radiation light 33b (I3) of an LED 33, a radiation light 34b (I4) of an LED 34, and a radiation light 35b (I5) of an LED 35 are 395 nm, 405 nm, 415 nm, and 425 nm, respectively. FIG. 14 is a graph illustrating spectral powers of the radiation lights (Iwb, I1, I2, I3, I4, and I5) used in the fourth embodiment. Weighting coefficients W2 to W5 of the excitation lights I2 to I5 are set by the setting method 1 as in the third embodiment, and only a weighting coefficient W1 of the excitation light I1 is set by the setting method 3. By this, a spectral power distribution Id2($\lambda$) of an illumination light Id2 synthesized by W2·I2($\lambda$)+W3·I3($\lambda$)+W4·I4($\lambda$)+W5·I5($\lambda$) approximates D50 at 400 to 430 nm as illustrated in FIG. 5. Each of all the illumination lights (four illumination lights) forming the illumination light Id2 is any one of the five excitation lights I1 to I5, but it is sufficient that at least one of a plurality of illumination lights is any one of a plurality of excitation lights.

Figure 15:
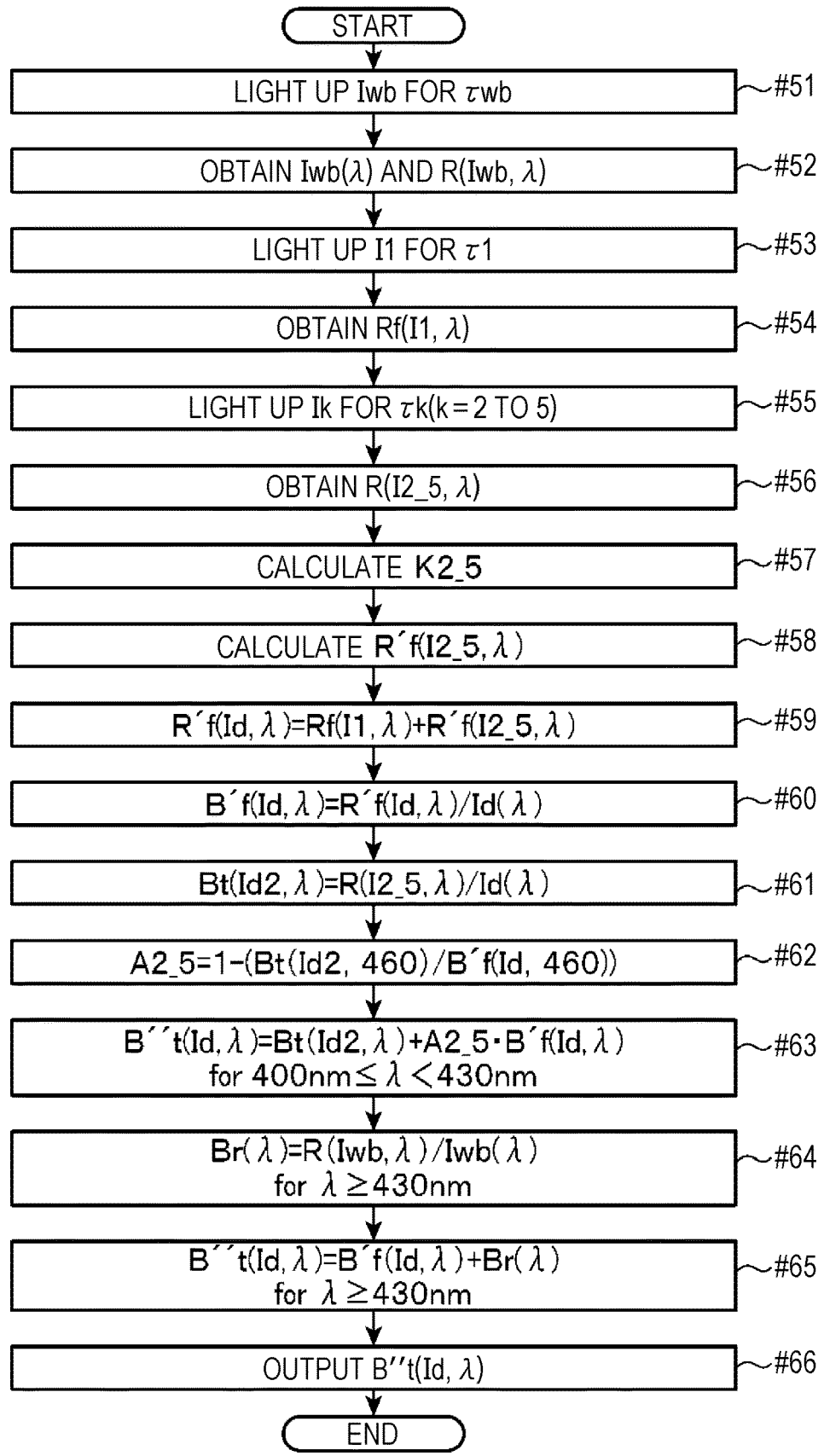
FIG. 15 is a flowchart illustrating a method for measuring spectral radiation characteristics of a fluorescence whitened sample according to the fourth embodiment.

FIG. 15 is a flowchart illustrating a method for measuring spectral radiation characteristics of a fluorescence whitened sample according to the fourth embodiment. Herein also, weighting of linear combination is performed by controlling a lighting time $\tau k$ of the LED. The lighting time $\tau k$ of an excitation light Ik and a lighting time $\tau wb$ of the illumination light Iwb based on a weighting coefficient Wk are provided in advance.

A control arithmetic device 10 lights up the light source (white LED 1) of the illumination light Iwb for the time $\tau wb$ (#51).

The control arithmetic device 10 obtains a spectral power distribution Iwb($\lambda$) of the illumination light Iwb and a spectral power distribution R(Iwb,$\lambda$) of a sample radiation light by the illumination light Iwb from a dual channel spectrometer 9 (#52).

The control arithmetic device 10 lights up a light source (LED) of the excitation light I1 having the central wavelength of 355 nm for a time $\tau 1$ (#53).

The control arithmetic device 10 obtains a spectral power distribution R(I1,$\lambda$) (=Rf(I1,$\lambda$)) of a sample radiation light by the excitation light I1 (#54).

The control arithmetic device 10 lights up a light source (LED) of the excitation light I2 having the central wavelength of 395 nm for a time $\tau 2$, a light source (LED) of the excitation light I3 having the central wavelength of 405 nm for a time $\tau 3$, a light source (LED) of the excitation light I4 having the central wavelength of 415 nm for a time $\tau 4$, and a light source (LED) of the excitation light I5 having the central wavelength of 425 nm for a time $\tau 5$ (#55).

The control arithmetic device 10 obtains a spectral power distribution R(I2_5,$\lambda$) of a sample radiation light by the excitation lights I2+I3+I4+I5 (#56).

The control arithmetic device 10 obtains a power coefficient K2_5 by equation (8) (#57).

The control arithmetic device 10 obtains an approximation R'f(I2_5,$\lambda$) of a spectral power distribution Rf(I2_5,$\lambda$) of fluorescence by an excitation light I2_5 by K2_5, and equations (9a) and (9b) (#58).

The control arithmetic device 10 adds R(I1,$\lambda$) and an approximation R'(I2_5,$\lambda$) to obtain an approximation R'f(Id,$\lambda$) of a spectral power distribution Rf(Id,$\lambda$) of fluorescence by a standard illumination light Id (#59).

The control arithmetic device 10 obtains an approximation B'f(Id,$\lambda$) of a fluorescence spectral emissivity coefficient Bf(Id,$\lambda$) by the standard illumination light Id by the approximation R'f(Id,$\lambda$), a spectral power distribution Id($\lambda$) of the standard illumination light Id, and equation (7) (#60).

The control arithmetic device 10 obtains a total spectral emissivity coefficient Bt(Id2,$\lambda$) of an overlapping range by the overlapping range illumination light Id2 using equation (19) (#61). The overlapping range is 400 nm$\leq\lambda<$430 nm. The overlapping range illumination light Id2 approximates D50.

The control arithmetic device 10 sets $\lambda r3=460$ nm, and obtains a power coefficient A2_5 using equation (21) (#62).

The control arithmetic device 10 obtains an approximation B"t(Id,$\lambda$) of a total spectral emissivity coefficient Bt(Id,$\lambda$) of the overlapping range by the standard illumination light Id using equation (20a) (#63).

The control arithmetic device 10 obtains a spectral reflectivity coefficient Br($\lambda$) outside the overlapping range by using equation (20c) (#64). Outside the overlapping range is $\lambda \geq 430$ nm.

The control arithmetic device 10 obtains an approximation B"t(Id,$\lambda$) of a total spectral emissivity coefficient Bt(Id, $\lambda$) outside the overlapping range by the standard illumination light Id using equation (20b) (#65).

The control arithmetic device 10 outputs the approximation B"t(Id,$\lambda$) in an entire visible range, that is, the approximations B"t(Id,$\lambda$) and B"t(Id,$\lambda$) of the overlapping range and outside the overlapping range, respectively (#66).

In a case of scanning and measuring a large number of printing patches for evaluating a printer, a short measuring time is required. In this embodiment, since the excitation lights I2 to I5 are simultaneously lighted up (a plurality of excitation lights Ik is simultaneously applied), the measuring time is shortened.

Fifth Embodiment

Figure 16:
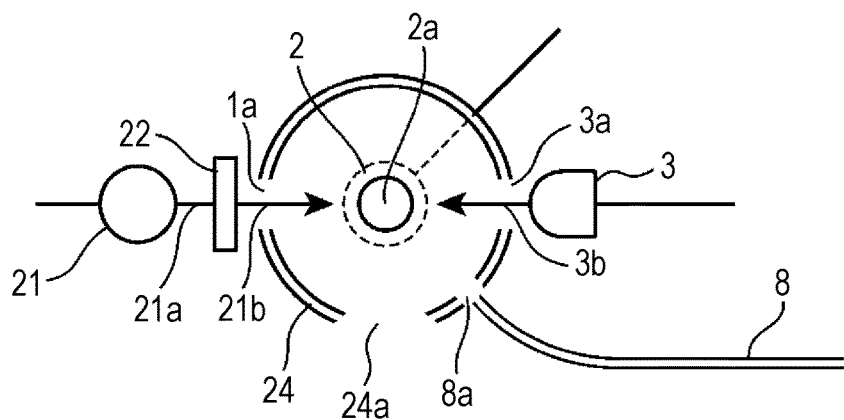
FIG. 16 is an illustrative diagram for explaining a relationship between a small integrating sphere and a radiation light incident on the small integrating sphere in an illumination light receiving system of a fifth embodiment.
Figure 17:
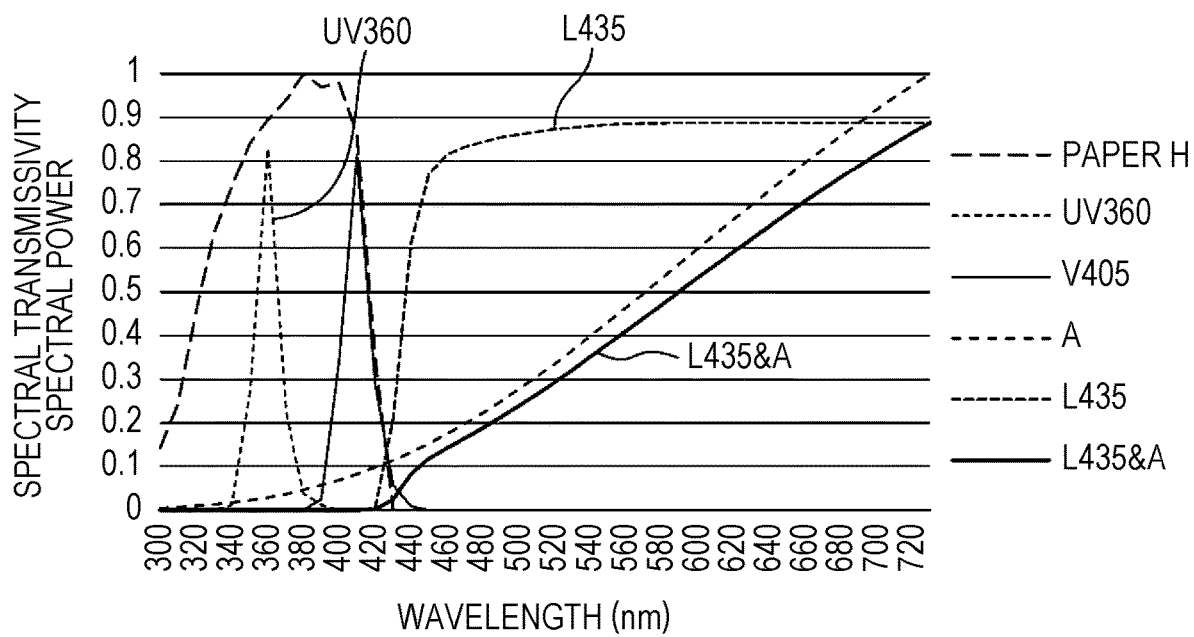
FIG. 17 is a graph for explaining optical characteristics of a white light source and a short wavelength cut filter.

A fifth embodiment is described. The fifth embodiment differs from the first to fourth embodiments in an illumination optical system. FIG. 16 is an illustrative diagram for explaining a relationship between a small integrating sphere and a radiation light incident on the small integrating sphere in an illumination light receiving system of the fifth embodiment. A small integrating sphere 24 illustrated in FIG. 16 is different from the small integrating sphere 24 illustrated in FIG. 9 in that a white light source 21 and a short wavelength cut filter 22 are provided in place of a white LED 1. The white light source 21 (for example, an incandescent lamp) has a power in an entire visible range. In the first to fourth embodiments, a radiation light of a blue-excited white LED is a component Ivis2 which does not excite fluorescence of a visible range illumination light Ivis. On the other hand, in the fifth embodiment, as illustrated in FIG. 16, a radiation light 21a of the white light source 21 transmitted through the short wavelength cut filter 22 is allowed to be incident on the small integrating sphere 24. FIG. 17 is a graph for explaining optical characteristics of the white light source 21 and the short wavelength cut filter 22. The graph illustrates a relative spectral power distribution (A in the drawing) of an incandescent lamp (illuminant A) with color temperature of 2855.6 K, a spectral transmissivity (L435) of a sharp cut filter L435 with a cutoff wavelength of 435 nm, and a spectral power distribution (L435 & A) of the illumination light obtained by combining them. This graph also illustrates a spectral quantum efficiency for 440 nm fluorescence of fluorescence whitened paper (Paper H).

Embodiments may also be provided with a measuring range illuminating unit. This is to be described. The measuring range illuminating unit illuminates the fluorescence whitened sample with a measuring range illumination light Ivis having a power in an entire measuring range (400 to 700 nm). A control arithmetic unit (control arithmetic device 10) lights up the measuring range illuminating unit, allow a sample radiation light spectroscopic unit (dual channel spectrometer 9) to measure a spectral distribution Rr(Ivis,λ) of a sample reflected light by the measuring range illumination light Ivis, obtains an approximation B'r(λ) of a spectral reflectivity coefficient Br(λ) from a spectral power distribution Ivis(λ) of the measuring range illumination light and the spectral power distribution Rr(Ivis,λ) of the sample reflected light (equation (16)), and obtains an approximation B't(Id,λ) of a total spectral emissivity coefficient Bt(Id,λ) by a standard illumination light by the sum of the approximation B'r(λ) and an approximation B'f(Id,λ) of a fluorescence spectral emissivity coefficient Bf(Id,λ) by the standard illumination light.

A first example of the measuring range illuminating unit includes a blue-excited white LED (white LED 1) and one or more monochromatic LEDs (purple LED 3) having a power in a measuring range where the blue-excited white LED does not have power, and the measuring range illumination light Ivis is formed of a radiation light of the blue-excited white LED and a radiation light of one or more monochromatic LEDs. A second example of the measuring range illuminating unit includes a white light source (white light source 21), a fluorescence excitation wavelength band cut filter (short wavelength cur filter 22), and one or more monochromatic LEDs having power in a fluorescence excitation light wavelength band (violet LED 3 illustrated in FIG. 16, and UV360 and V405 illustrated in FIG. 17), and the measuring range illumination light Ivis is formed of a radiation light of the white light source passing through the fluorescence excitation wavelength band cut filter and one or more monochromatic LEDs.

Figure 18:
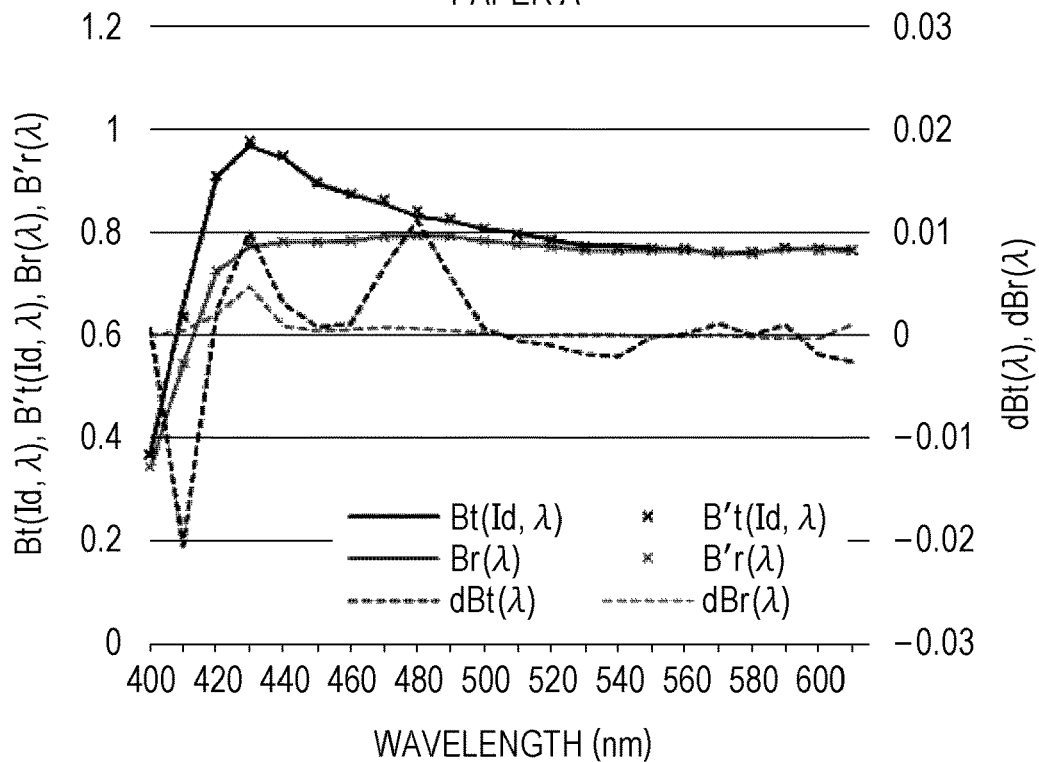
FIG. 18 is a graph illustrating spectral radiation characteristics of a first example of fluorescence whitened paper.
Figure 19:
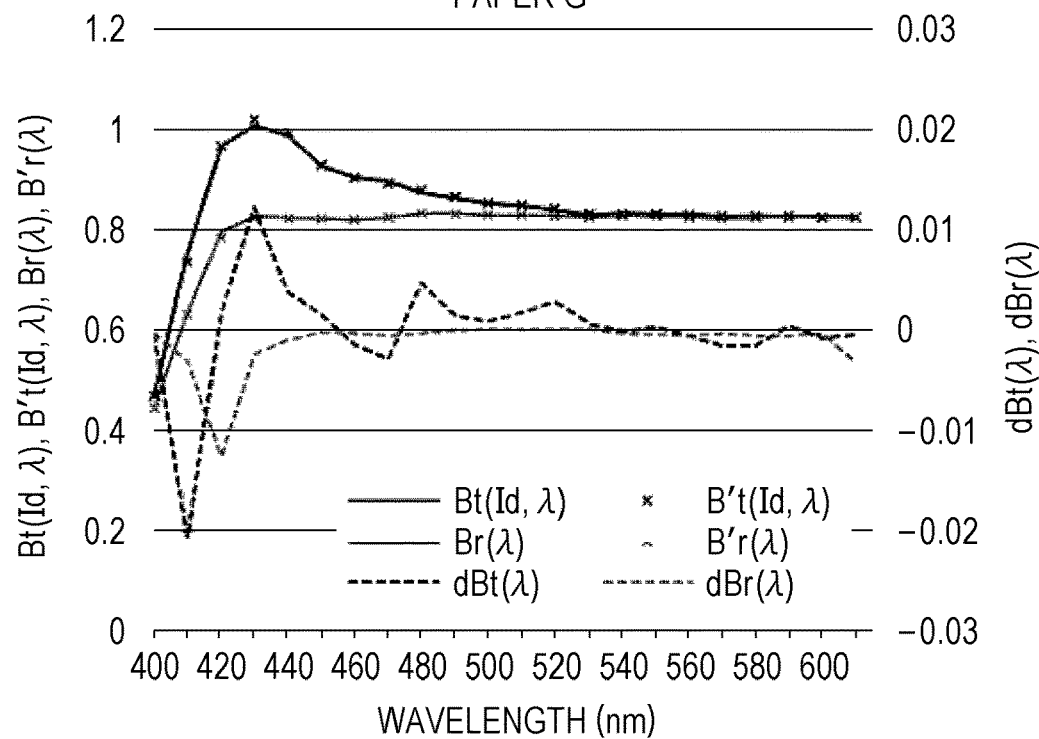
FIG. 19 is a graph illustrating spectral radiation characteristics of a second example of the fluorescence whitened paper.
Figure 20:
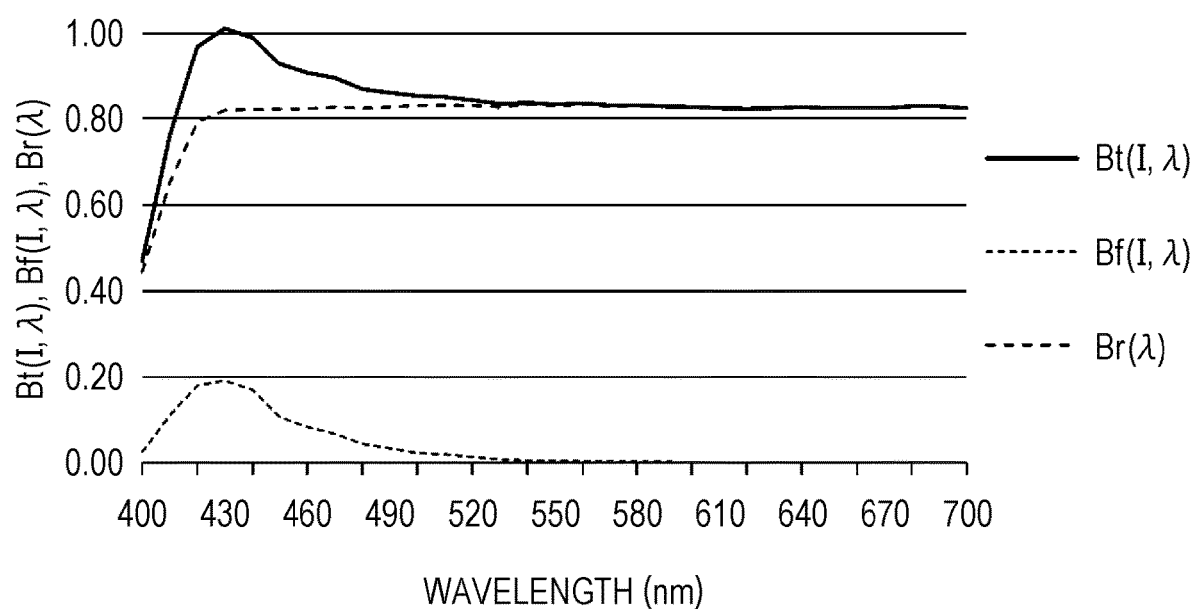
FIG. 20 is a graph illustrating a relationship among a total spectral emissivity coefficient Bt(I,λ), a spectral reflectivity coefficient Br(λ), and a fluorescence spectral emissivity coefficient Bf(I,λ).

Next, effects of the embodiment are described by data. FIG. 18 is a graph illustrating spectral radiation characteristics of fluorescence whitened paper (paper A). FIG. 19 is a graph illustrating spectral radiation characteristics of fluorescence whitened paper (paper G). The wavelength is plotted along the abscissa axis of these graphs. Bt(Id,λ), B't(Id,λ), Br(λ), and B'r(λ) are plotted along the left ordinate axis of the graph, and dBt(λ) and dBr(λ) are plotted along the right ordinate axis. B't(Id,λ) and B'r(λ) are measured values measured by the method for measuring the embodiment. Bt(Id,λ) and Br(λ) are reference values. dBt(λ) indicates a difference between B't(Id,λ) and Bt(Id,λ). dBr(λ) indicates a difference between B'r(λ) and Br(λ). In any case, it may be seen that the measured value coincides well to a reference value. As for the spectral reflectivity coefficient, a reflectivity coefficient of 420 nm or shorter which cannot be obtained by a conventional method (method in accordance with ISO 2470) of removing a component of 420 nm or shorter of the illumination light is obtained.

Summary of Embodiments

[1] One aspect of an embodiment is a method for measuring spectral radiation characteristics of a fluorescence whitened sample illuminated with a standard illumination light Id, the method provided with obtaining an approximation B'f(Id,λ) of a fluorescence spectral emissivity coefficient Bf(Id,λ) by the standard illumination light Id at following first to third steps from spectral power distributions R(Ik,λ) of sample radiation lights generated when the fluorescence whitened sample is sequentially illuminated with a plurality of excitation lights Ik (k=1 to n) having different spectral power distributions and a spectral power distribution Id(λ) of the standard illumination light Id.

First step: Spectral power distributions Rf(Ik,λ) of fluorescence are obtained from the spectral power distributions R(Ik,λ) by respective excitation lights Ik.

Second step: The spectral power distributions Rf(Ik,λ) of fluorescence by the respective excitation lights Ik are linearly combined with a given weighting coefficient Wk, and an approximation R'f(Id,λ) of a spectral power distribution Rf(Id,λ) of fluorescence by the standard illumination light Id is obtained by following equation (6).

[Math. 28]

$$R'_f(I_d, \lambda) = \sum_k W_k \cdot R_f(I_k, \lambda) \qquad \text{Equation (6)}$$

Third step: The approximation B'f(Id,λ) is obtained by following equation (7) from the approximation R'f(Id,λ) and the spectral power distribution Id(λ) of the standard illumination light Id.

[Math. 29]

$$B'_f(I_d, \lambda) = \frac{R'_f(I_d, \lambda)}{I_d(\lambda)} \qquad \text{Equation (7)}$$

These steps make it possible to improve accuracy of the approximation B'f(Id,λ) of the fluorescence spectral emissivity coefficient Bf(Id,λ) by the standard illumination light Id for the fluorescence whitened paper having various bispectral fluorescence emissivity coefficients.

[2] In the above-described configuration, the plurality of excitation lights Ik is monochromatic excitation lights.

According to this configuration, a weighted linear combination of the spectral power distributions Rf(Ik,λ) of fluorescence by the plurality of excitation lights Ik is obtained, and it is possible to improve accuracy of the approximation R'f(Id,λ) of spectral power distributions Rf(Id,λ) of fluorescence by various standard illumination lights Id.

[3] In the above-described configuration, the monochromatic excitation lights are monochromatic LED radiation lights.

According to this configuration, the monochromatic excitation light of sufficient power may be obtained with high efficiency and at a low cost.

[4] In the above-described configuration, a plurality of sets of weighting coefficients Wk corresponding to a plurality of standard illumination lights Id, respectively, is set, and the approximation R'f(Id,λ) is obtained by applying a set of weighting coefficients Wk corresponding to each standard illumination light Id (<measurement principle>[B]).

According to this configuration, the approximation R'f(Id, λ) of the spectral power distributions Rf(Id,λ) of fluorescence by a plurality of standard illumination lights Id may be obtained by one measurement.

[5] In the above-described configuration, the plurality of excitation lights Ik includes a first type of excitation light Ik1 (monochromatic illumination light I1 having a central wavelength of 360 nm) outside an overlapping range of a reflected light range and a fluorescence range, and a second type of excitation light Ik2 (monochromatic illumination light I2 having a central wavelength of 405 nm) within the overlapping range, at the first step, a spectral power distribution Rf(Ik1,λ) of fluorescence by the first type of excitation light Ik1 is obtained from a spectral power distribution $R(Ik1,\lambda)$ of a sample radiation light by the first type of excitation light Ik1 (since the central wavelength of the first type of excitation light Ik1 is outside the overlapping range, $Rf(Ik1,\lambda)$ is equal to $R(Ik1,\lambda)$), an approximation $R'f(Ik2,\lambda)$ of at least a part of a spectral power distribution $Rf(Ik2,\lambda)$ of fluorescence by the second type of excitation light Ik2 is estimated on the basis of the spectral power distribution $R(Ik1,\lambda)$ of the sample radiation light by the first type of excitation light Ik1 (within the overlapping range, an approximation $R'f(I2,\lambda)$ of a spectral power distribution $Rf(I2,\lambda)$ of fluorescence by the monochromatic illumination light I2 is obtained by using equation (9a)), and a remaining part is obtained from the spectral power distribution $R(Ik2,\lambda)$ of the sample radiation light by the second type of excitation light Ik2 (outside the overlapping range, equation (9b) is used. Note that, it is not $R(I2,\lambda)$ but $Rf(I2,\lambda)$ in equation (9b), a coefficient K expressed in equation (8) may be reworded as a ratio between spectral power distributions $R(I1,\lambda r1)$ and $R(I2,\lambda r1)$ of sample radiation lights by the monochrome illumination lights I1 and I2 at a reference wavelength $\lambda r1$. Therefore, $Rf(I2,\lambda)$ in equation (9b) may be rewarded as $R(I2,\lambda)$).

According to this configuration, it is possible to improve accuracy of the approximation $R'f(Ik2,\lambda)$ of the spectral power distribution $Rf(Ik2,\lambda)$ of fluorescence by the second type of excitation light Ik2 even in the wavelength range in which the spectral power distribution of the sample radiation light by the second type of excitation light Ik2 $R(Ik2,\lambda)=R'f(Ik2,\lambda)$ is not satisfied.

[6] In the above-described configuration, the approximation $R'f(Ik2,\lambda)$ of at least a part of the spectral power distribution $Rf(Ik2,\lambda)$ of fluorescence by the second type of excitation light Ik2 as the estimation at following fourth to sixth steps.

Fourth step: A ratio K of powers of the sample radiation lights by the first and second types of excitation lights Ik1 and Ik2 at one or more reference wavelengths $\lambda r1$ outside the overlapping range is obtained by following equation (22). Equation (22) corresponds to equation (8).

[Math. 30]

$$K = \frac{R(I_{k2},\lambda_{r1})}{R(I_{k1},\lambda_{r1})} \quad \text{Equation (22)}$$

Fifth step: A correction coefficient $C(\lambda)$ reflecting that a fluorescence wavelength $\lambda$ is longer than an excitation wavelength $\mu$ is obtained.

Sixth step: The approximation $R'f(Ik2,\lambda)$ is obtained by following equation (23) from the spectral power distribution $R(Ik1,\lambda)$ of the sample radiation light by the first type of excitation light Ik1, the ratio K of the powers, and the correction coefficient $C(\lambda)$. Equation (23) corresponds to equation (9a).

[Math. 31]

$$R'_f(I_{k2},\lambda) = R(I_{k1},\lambda) \cdot K \cdot C(\lambda) \quad \text{Equation (23)}$$

According to this configuration, it is possible to improve accuracy of the approximation $R'f(Ik2,\lambda)$ of the spectral power distribution $Rf(Ik2,\lambda)$ of fluorescence by the second type of excitation light Ik2 also in the above-described part.

[7] In the above-described configuration, the spectral power distribution of the second type of excitation light Ik2 is obtained from $Ik2(\mu)$, and the correction coefficient $C(\lambda)$ is obtained by following equation (24). Equation (24) corresponds to equation (10).

[Math. 32]

$$C(\lambda) = 1 - \frac{\sum_{\mu=\lambda}^{\infty} I_{k2}(\mu)}{\sum_{\mu=0}^{\infty} I_{k2}(\mu)} \quad \text{Equation (24)}$$

According to this configuration, it is possible to improve accuracy of the approximation $R'f(Ik2,\lambda)$ of the spectral power distribution $Rf(Ik2,\lambda)$ of fluorescence by the second type of excitation light Ik2 also in the above-described part.

[8] In the above-described configuration, the part includes the overlapping range.

According to this configuration, it is possible to improve accuracy of the approximation $R'f(Ik2,\lambda)$ of the spectral power distribution $Rf(Ik2,\lambda)$ of fluorescence by the second type of excitation light Ik2 also in the wavelength range in which the reflected light and fluorescence of the second type of excitation light Ik2 overlap.

[9] In the above-described configuration, powers of the plurality of excitation lights Ik (k=1 to n) are proportional to the weighting coefficient Wk (third embodiment).

According to this configuration, since a plurality of excitation lights may be simultaneously applied, a measuring time may be shortened.

[10] In the above-described configuration, powers of the plurality of excitation lights Ik (k=1 to n) are controlled by an irradiation time (third embodiment).

According to this configuration, it is possible to control the excitation light power with a simple LED driving circuit.

[11] In the above-described configuration, two or more excitation lights Ik (excitation lights I2 to I4) out of the plurality of excitation lights Ik (k=1 to n) are simultaneously applied (third embodiment).

According to this configuration, the measuring time may be shortened.

[12] In the above-described configuration, the weighting coefficient Wk for setting the powers of the plurality of excitation lights Ik (k=1 to n) is obtained on the basis of a spectral power distribution $Ik(\mu)$ of the excitation light Ik obtained at most recent measurement (first embodiment).

According to this configuration, prior measurement of the spectral power distribution $Ik(\mu)$ of the excitation light Ik for setting the Wk becomes unnecessary. Especially, the effect is large in continuous measurement of a large number of samples.

[13] In the above-described configuration, each of the plurality of excitation lights Ik (k=1 to n) is a radiation light of a monochrome LED driven at constant current, and the spectral power distribution $Ik(\mu)$ of each of the plurality of excitation lights Ik is obtained on the basis of a forward voltage when driving the monochrome LED and known correlation characteristics of forward voltage-spectral power distribution (first embodiment).

According to this configuration, even if a plurality of monochromatic LEDs is simultaneously lighted up, it is possible to estimate the spectral power distribution $Ik(\mu)$ of each excitation light Ik from the forward voltage of each LED individually detected and provide the same for Wk setting.

[14] In the above-described configuration, the weighting coefficient Wk is set such that a spectral power distribution I'd(λ) of a synthetic excitation light I'd obtained by linearly combining the spectral power distributions of the plurality of excitation lights Ik by following equation (12) approximates the spectral power distribution Id(λ) of the standard illumination light Id (<measurement principle>[B] (setting method 1).

[Math. 33]

$$I'_d(\lambda) = \sum_k W_k \cdot I_k(\lambda) \quad \text{Equation (12)}$$

According to this configuration, the weighting coefficient Wk for a large number of excitation lights Ik may be set on the basis of the spectral power distribution Ik(λ) of the excitation lights Ik and the spectral power distribution Id(λ) of the standard illumination light Id.

[15] In the above-described configuration, the weighting coefficient Wk is set at following seventh and eighth steps from the spectral power distributions Ik(λ) of the plurality of excitation lights Ik, the spectral power distribution Id(λ) of the standard illumination light Id, and a plurality of different bispectral fluorescence emissivity coefficients FT(μ,λ) (T=1 to N, μ represents an excitation wavelength and λ represents a fluorescence wavelength) (<measurement principle>[B] (setting method 2).

Seventh step: Spectral power distributions Rf,T(Ik,λ) of fluorescence by the plurality of excitation lights Ik and a spectral power distribution Rf,T(Id,λ) of fluorescence by the standard illumination light Id are obtained by following equations (25) and (26) from the plurality of bispectral fluorescence emissivity coefficients FT(μ,λ), the spectral power distributions Ik(μ) of the plurality of excitation lights Ik, and a spectral power distribution Id(λ) of the standard illumination light Id.

[Math. 34]

$$R_{f,T}=(I_k,\lambda)=\int I_k(\mu)F_T(\mu,\lambda)d\mu, \quad \text{Equation (25)}$$

[Math. 35]

$$R_{f,T}=(I_d,\lambda)=\int I_d(\mu)F_T(\mu,\lambda)d\mu, \quad \text{Equation (26)}$$

Eighth step: The weighting coefficient Wk is set such that a spectral power distribution R'f,T(Id,λ) of synthetic fluorescence obtained by linearly combining the spectral power distributions Rf,T(Ik,λ) of fluorescence by the plurality of excitation lights Ik by following equation (27) approximates the spectral power distribution Rf,T(Id,λ) of fluorescence by the standard illumination light Id for all of the plurality of bispectral fluorescence emissivity coefficients FT(μ, λ).

[Math. 36]

$$R'_{f*T}(I_d, \lambda) = \sum_k W_k \cdot R_{f*T}(I_k, \lambda) \quad \text{Equation (27)}$$

According to this configuration, the approximation R'f,T(Id,λ) of the spectral power distribution Rf,T(Id,λ) of fluorescence by the standard illumination light Id may be synthesized also in a case where the number of excitation lights Ik is small.

[16] In the above-described configuration, the weighting coefficient Wk is set at following ninth and tenth steps from the spectral power distributions Ik(λ) of the plurality of excitation lights Ik, the spectral power distribution Id(λ) of the standard illumination light Id, and a plurality of different spectral quantum efficiencies FT(μ,λr2) (T=1 to N, μ represents an excitation wavelength) for fluorescence at a reference wavelength λr2 (<measurement principle>[B] (setting method 3).

Ninth step: Fluorescence powers Rf,T(Ik,λr2) at the reference wavelength λr2 by the plurality of excitation lights Ik and fluorescence power Rf,T(Id,λr2) at the reference wavelength λr2 by the standard illumination light Id are obtained by following equations (28) and (29) from the plurality of spectral quantum efficiencies FT(μ,λr2), the spectral power distributions Ik(μ) of the plurality of excitation lights Ik, and the spectral power distribution Id(μ) of the standard illumination light Id.

[Math. 37]

$$R_{f,T}=(I_d,\lambda_{r2})=\int I_d(\mu)F_T(\mu,\lambda_{r2})d\mu, \quad \text{Equation (28)}$$

[Math. 38]

$$R_{f,T}=(I_k,\lambda_{r2})=\int I_k(\mu)F_T(\mu,\lambda_{r2})d\mu, \quad \text{Equation (29)}$$

Tenth step: The weighting coefficient Wk is set such that a synthetic fluorescence power R'f,T(Id,λr2) obtained by linearly combining the fluorescence powers Rf,T(Ik,λr2) by following equation (30) approximates the fluorescence power Rf,T(Id,λr2) by the standard illumination light Id for all of the plurality of spectral quantum efficiencies FT(μ, λr2).

[Math. 39]

$$R'_{f*T}(I_d, \lambda_{r2}) = \sum_k W_k \cdot R_{f*T}(I_k, \lambda_{r2}) \quad \text{Equation (30)}$$

According to this configuration, an appropriate weighting coefficient Wk may be set with a much smaller amount of data and shorter processing time than those in the method in [12].

[17] A part of the weighting coefficients Wk set by the method in [14] is reset by the method in [15] or [16].

According to this configuration, even in a case where there is a wavelength range in which the excitation light Ik does not exist, and the spectral power distribution Id(λ) of the standard illumination light Id cannot be sufficiently approximated by this, it is possible to set an appropriate weighting coefficient Wk.

[18] In the above-described configuration, the bispectral fluorescence emissivity coefficients FT(μ,λ) of the fluorescence whitened sample to be measured are classified into a plurality of types (FIG. 4), the plurality of different bispectral fluorescence emissivity coefficients being the plurality of types of bispectral fluorescence emissivity coefficients, or spectral quantum efficiencies FT(μ,λr2) for fluorescence at the reference wavelength λr2 of the fluorescence whitened sample to be measured are classified into a plurality of types, the plurality of different spectral quantum efficiencies being the plurality of types of spectral quantum efficiencies.

According to this configuration, the set weighting coefficient may provide a highly accurate fluorescence spectral emissivity coefficient for the classified sample to be measured (measurement target).

[19] In the above-described configuration, an approximation B'r($\lambda$) of a spectral reflectivity coefficient Br($\lambda$) is obtained from a spectral power distribution Ivis($\lambda$) of a measuring range illumination light Ivis having a power in an entire measuring range and a spectral power distribution Rr(Ivis,$\lambda$) of a sample reflected light by the measuring range illumination light Ivis (first half of equation (16)), and an approximation B't(Id,$\lambda$) of a total spectral emissivity coefficient Bt(Id,$\lambda$) by the standard illumination light Id is obtained by a sum of the approximation B'r($\lambda$) and the approximation B'f(Id,$\lambda$).

According to this configuration, it is possible to improve the accuracy of the approximation of the total spectral emissivity coefficient for the fluorescence whitened paper having various bispectral fluorescence emissivity coefficients. The entire measuring range is, for example, the wavelength range (visible range) of 400 to 700 nm.

[20] In the above-described configuration, a spectral reflectivity coefficient Br($\lambda$) outside the overlapping range is obtained from a spectral power distribution Ivis1($\lambda$) of an illumination light Ivis1 outside the overlapping range having a power in the entire measuring range outside the overlapping range and a spectral power distribution Rr(Ivis1)) of a sample reflected light by the illumination light Ivis1 outside the overlapping range (equation (20c)), an approximation B''t(Id,$\lambda$) of a total spectral emissivity coefficient outside the overlapping range by the standard illumination light Id is provided by a sum of the spectral reflectivity coefficient Br($\lambda$) and the approximation B'f(Id,$\lambda$) (equation (20b)), and the approximation B''t(Id,$\lambda$) of the total spectral emissivity coefficient of the overlapping range by the standard illumination light Id is obtained by a sum of a total spectral emissivity coefficient Bt(Id2,$\lambda$) of the overlapping range by the overlapping range illumination light Id2 obtained from a spectral power distribution Id2($\lambda$) of an overlapping range illumination light Id2 having a spectral power distribution approximating the standard illumination light Id in the overlapping range and a spectral power distribution R(Id2,$\lambda$) of a sample radiation light by the overlapping range illumination light Id2 (equation (19)) and a fluorescence spectral emissivity coefficient Bf(Id1,$\lambda$) by an excitation component Id1 other than an overlapping range component of the standard illumination light Id (first half of equation (20a)).

According to this configuration, it is possible to avoid an approximation error of the overlapping range which tends to be larger and improve the accuracy of the approximation of the total spectral emissivity coefficient for the fluorescence whitened paper having various bispectral fluorescence emissivity coefficients.

[21] In the above-described configuration, the overlapping range illumination light Id2 having a spectral power distribution approximating the standard illumination light Id in the overlapping range is provided by weighted linear combination of a plurality of illumination lights (fourth embodiment: illumination light Id2 synthesized by W2·I2($\lambda$)+W3·I3($\lambda$)+W4·I4($\lambda$)+W5·I5($\lambda$).

Since the overlapping range is limited, it is possible to obtain an approximating illumination light with sufficient accuracy by lighting up a small number of monochromatic LEDs with an appropriate power, for example.

[22] In the above-described configuration, at least one of the plurality of illumination lights is any of the plurality of excitation lights Ik.

According to this configuration, it is possible to suppress the number of illumination lights required as an entire illumination system.

[23] In the above-described configuration, the Bf(Id1,$\lambda$) being a component not by the overlapping range illumination light Id2 of the approximation B'f(Id,$\lambda$) is obtained at following eleventh and twelfth steps.

Eleventh step: A power coefficient A is obtained by following equation (21) from a total spectral emissivity coefficient Bt(Id2,$\lambda$r3) by the overlapping range illumination light Id2 at one or more reference wavelengths $\lambda$r3 not affected by a reflected light of the overlapping range illumination light Id2, and an approximation B'f(Id,$\lambda$r3) of a fluorescence emissivity coefficient by the standard illumination light Id.

[Math. 40]

$$A = 1 - \frac{B_t(I_{d2}, \lambda_{r3})}{B'_f(I_d, \lambda_{r3})}$$ Equation (21)

Twelfth step: The Bf(Id1,$\lambda$) is obtained by following equation (35) from the approximation B'f(Id,$\lambda$) of the fluorescence spectral emissivity coefficient by the standard illumination light Id and the power coefficient A.

[Math. 41]

$$B_f(I_{d1},\lambda) = A \cdot B'_f(I_d,\lambda)$$ Equation (35)

According to this configuration, it is possible to avoid the approximation error of the overlapping range which tends to be large and to provide highly accurate approximation of the total spectral emissivity coefficient by simple operation.

[24] In the above-described configuration, the spectral power distribution Rr(Ivis,$\lambda$) of the sample reflected light is obtained by subtracting a spectral power distribution Rf(Ivis,$\lambda$) of fluorescence by the measuring range illumination light Ivis from a spectral power distribution R(Ivis,$\lambda$) of a sample radiation light by the measuring range illumination light Ivis (equation (16)).

By using the spectral power distribution Rr(Ivis,$\lambda$) of the sample reflected light by the measuring range illumination light Ivis, the accuracy of the approximation B't(Id,$\lambda$) of the total spectral emissivity coefficient Bt(Id,$\lambda$) by the standard illumination light Id may be improved.

[25] In the above-described configuration, the measuring range illumination light Ivis is formed of a first measuring range illumination light Ivis1 not including an excitation range and a second measuring range illumination light Ivis2 including the excitation range, and the approximation B'r($\lambda$) of the spectral reflectivity coefficient Br($\lambda$) of the fluorescence whitened sample is obtained by following thirteenth to sixteenth steps from a spectral power distribution Ivis1($\lambda$) of the first measuring range illumination light Ivis1 and a spectral power distribution R(Ivis1,$\lambda$) of the sample radiation light by the first measuring range illumination light, and a spectral power distribution Ivis2($\lambda$) of the second measuring range illumination light Ivis2 and a spectral power distribution R(Ivis2,$\lambda$) of the sample radiation light by the second measuring range illumination light.

Thirteenth step: The spectral power distribution Ivis($\lambda$) of the measuring range illumination light Ivis is provided by a sum of the spectral power distributions Ivis1($\lambda$) and Ivis2($\lambda$) of the first and second measuring range illumination lights (equation (17)).

Fourteenth step: The spectral power distribution R(Ivis,$\lambda$) of the sample radiation light by the measuring range illumination light Ivis is provided by a sum of R(Ivis1,λ) and R(Ivis2,λ) by the first and second measuring range illumination lights (equation (18)).

Fifteenth step: A spectral power distribution Rf(Ivis2,λ) of fluorescence by the second measuring range illumination light Ivis2 is obtained.

Sixteenth step: The approximation B'r(λ) is obtained by following equation (31) while setting the Rf(Ivis2,λ) as Rf(Ivis,λ).

[Math. 42]

$$B'_r(\lambda) = \frac{R(I_{VIS}, \lambda) - R_f(I_{VIS}, \lambda)}{I_{VIS}(\lambda)} \quad \text{Equation (31)}$$

It is possible to obtain the approximation of the total spectral emissivity coefficient with high accuracy using the approximation B'r(λ) obtained by this configuration. Since the first measuring range illumination light Ivis1 does not excite the fluorescence, Rf(Ivis2,λ) is equal to Rf(Ivis,λ).

[26] In the above-described configuration, the spectral power distribution Rf(Ivis2,λ) of fluorescence by the second measuring range illumination light is obtained at following seventeenth to twentieth steps from the spectral power distribution Ivis2(λ) of the second measuring range illumination light, the spectral power distribution R(Ivis2,λ) of the sample radiation light by the second measuring range illumination light, the spectral power distribution Ik1(λ) of the first type of excitation light outside the overlapping range of the reflected light range and the fluorescence range, and the spectral power distribution R(Ik1,λ) of the sample radiation light by the first type of excitation light.

Seventeenth step: A component outside the overlapping range of the spectral power distribution Rf(Ivis2,λ) of fluorescence by the second measuring range illumination light is obtained from the spectral power distribution R(Ivis2,λ) of the sample radiation light by the second measuring range illumination light. Since Rf(Ivis2,λ) equals to R(Ivis2,λ) outside the overlapping range, R(Ivis2,λ) may be made Rf(Ivis2,λ)

Eighteenth step: A ratio K' between a spectral power distribution R(Ik1,λr4) of the sample radiation light by the first type of excitation light and a spectral power distribution R(Ivis2,λr4) of the sample radiation light by the second measuring range illumination light at one or more reference wavelengths λr4 outside the overlapping range is obtained by following equation (32).

[Math. 43]

$$K' = \frac{R(I_{VIS2}, \lambda_{r4})}{R(I_{k1}, \lambda_{r4})} \quad \text{Equation (32)}$$

Nineteenth step: A correction coefficient C'(λ) reflecting that the fluorescence wavelength λ is longer than the excitation wavelength μ is obtained.

Twentieth step: An approximation R'f(Ivis2,λ) of a component in the overlapping range of the spectral power distribution Rf(Ivis2,λ) of fluorescence by the second measuring range illumination light is obtained by following equation (33) from the spectral power distribution R(Ik1,λ) of the sample radiation light by the first type of excitation light, the power ratio K', and the correction coefficient C'(λ). In the overlapping range, the approximation R'f(Ivis2,λ) is regarded as Rf(Ivis2,λ)

[Math. 44]

$$R'_f(I_{VIS2},\lambda)=R(I_{k1},\lambda)\cdot K'\cdot C'(\lambda) \quad \text{Equation (33)}$$

It is possible to obtain the approximation of the total spectral emissivity coefficient with high accuracy using the approximation R'f(Ivis2,λ) obtained by this configuration. Equation (32) means equation (8). Equation (33) means equation (9a). Ivis2 corresponds to I2, Ik1 corresponds to I1, and λr4 corresponds to λr1.

[27] In the above-described configuration, the correction coefficient C'(λ) is obtained by following equation (34) from the spectral power distribution Ivis2(λ) of the second measuring range illumination light.

[Math. 45]

$$C'(\lambda) = 1 - \frac{\sum_{\mu=\lambda}^{\infty} I_{VIS2}(\mu)}{\sum_{\mu=0}^{\infty} I_{VIS2}(\mu)} \quad \text{Equation (34)}$$

According to this configuration, the accuracy of the approximation R'f(Ivis2,λ) of the fluorescence spectral power distribution by the second measuring range illumination light Ivis2 is improved. Equation (34) means equation (10).

[28] A device for measuring spectral radiation characteristics of a fluorescence whitened sample according to another aspect of the embodiment is provided with: a plurality of excitation light illuminating units for illuminating the fluorescence whitened sample with a plurality of excitation lights Ik (k=1 to n) having different spectral power distributions; a sample radiation light spectroscopic unit (dual channel spectroscope 9) for measuring spectral power distributions R(Ik,λ) of sample radiation lights being radiation lights radiated from the fluorescence whitened sample illuminated by the excitation lights Ik; and a control arithmetic unit, in which the control arithmetic unit sequentially lights up the plurality of excitation light illuminating units to allow the sample radiation light spectroscopic unit to measure the spectral power distributions R(Ik,λ) of the sample radiation lights, obtains spectral power distributions Rf(Ik,λ) of fluorescence from the spectral power distributions R(Ik,λ) of the sample radiation lights, obtains an approximation R'f(Id,λ) of a spectral power distribution Rf(Id,λ) of fluorescence by a standard illumination light Id by using the spectral power distributions Rf(Ik,λ) of fluorescence and a given weighting coefficient Wk by following equation (6)

[Math. 46]

$$R'_f(I_d, \lambda) = \sum_k W_k \cdot R_f(I_k, \lambda) \quad \text{Equation (6)}$$

and obtains an approximation B'f(Id,λ) of a fluorescence spectral emissivity coefficient Bf(Id,λ) by the standard illumination light Id from the approximation R'f(Id,λ) and a known spectral power distribution Id(λ) of the standard illumination light Id by following equation (7).

[Math. 47]

$$B'_f(I_d, \lambda) = \frac{R'_f(I_d, \lambda)}{I_d(\lambda)} \qquad \text{Equation (7)}$$

According to a second aspect of the present invention, it is possible to improve accuracy of an approximation B'f(Id, λ) of a fluorescence spectral emissivity coefficient Bf(Id,λ) by the standard illumination light Id for the fluorescence whitened paper having various bispectral fluorescence emissivity coefficients.

[29] In the above-described configuration, each of the plurality of excitation lights Ik is a radiation light of a monochromatic LED.

According to this configuration, a highly efficient excitation light illuminating unit may be realized at a low cost.

[30] In the above-described configuration, an excitation light spectroscopic unit (dual channel spectrometer 9) is further provided, in which the control arithmetic unit allows the excitation light spectroscopic unit to measure the spectral power distributions Ik(λ) of the excitation lights Ik, and obtains the weighting coefficient Wk on the basis of the spectral power distributions Ik(λ) (equation (12)).

According to this configuration, it is possible to set the weighting coefficient Wk corresponding to variation of the spectral power distribution Ik (λ) of the excitation light Ik.

[31] In the above-described configuration, a driving unit which drives the monochrome LED at a constant current, and a forward voltage measuring unit which measures a forward voltage of the monochrome LED at the time of driving are further provided, in which the control arithmetic unit estimates the spectral power distributions Ik(λ) of the excitation lights Ik on the basis of the forward voltage measured by the forward voltage measuring unit, and obtains the weighting coefficient Wk on the basis of the estimated spectral power distributions Ik(λ).

According to this configuration, it is possible to set the weighting coefficient Wk corresponding to the variation of the spectral power distribution Ik(λ) of the excitation light Ik without providing an excitation light spectroscopic unit.

[32] In the above-described configuration, a measuring range illuminating unit which illuminates the fluorescence whitened sample with a measuring range illumination light Ivis having a power in an entire measuring range is further provided, in which the control arithmetic unit lights up the measuring range illuminating unit to allow the sample radiation light spectroscopic unit to measure a spectral power distribution Rr(Ivis,λ) of a sample reflected light by the measuring range illumination light, obtains an approximation B'r(λ) of a spectral reflectivity coefficient Br(λ) from a spectral power distribution Ivis(λ) of the measuring range illumination light and the spectral power distribution Rr(Ivis,λ) of the sample reflected light (equation (16)), and obtains an approximation B't(Id,λ) of a total spectral emissivity coefficient Bt(Id,λ) by the standard illumination light Id by a sum of the approximation B'r(λ) and the approximation B'f(Id,λ) of the fluorescence spectral emissivity coefficient Bf(Id,λ) by the standard illumination light.

According to this configuration, it is possible to obtain a highly accurate approximation of the total spectral emissivity coefficient for fluorescence whitened paper having various bispectral fluorescence emissivity coefficients.

[33] In the above-described configuration, the measuring range illuminating unit includes a blue-excited white LED and one or more monochrome LEDs having a power in a measuring range where the blue-excited white LED does not have power, and the measuring range illumination light Ivis is formed of a radiation light of the blue-excited white LED and a radiation light of the one or more monochrome LEDs.

According to this configuration, highly efficient measuring range illumination means may be realized at a low cost.

[34] In the above-described configuration, the measuring range illuminating unit includes a white light source, a fluorescence excitation wavelength band cut filter, and one or more monochromatic LEDs having a power in a fluorescence excitation light wavelength band, and the measuring range illumination light Ivis is formed of a radiation light of the white light source passing through the fluorescence excitation wavelength band cut filter and the one or more monochromatic LEDs.

According to this configuration, it is possible to realize the measuring range illumination light having a spectral power distribution with less unevenness.

Although embodiments of the present invention are illustrated and described in detail, it is to be understood that such examples are illustrative only and not restrictive. The scope of the present invention should be construed by the language of appended claims.

The disclosure of JP 2017-054885 A filed on Mar. 21, 2017 is entirely incorporated herein by reference.

INDUSTRIAL APPLICABILITY

According to the present invention, it is possible to provide the method for measuring the spectral radiation characteristics of the fluorescence whitened sample and the device for measuring the spectral radiation characteristics of the fluorescence whitened sample.

The invention claimed is:

1. A method for measuring spectral radiation characteristics of a fluorescence whitened sample illuminated with a standard illumination light Id, the method comprising:

obtaining an approximation B'f(Id,λ) of a fluorescence spectral emissivity coefficient Bf(Id,λ) by the standard illumination light Id at following first to third steps from spectral power distributions R(Ik,λ) of sample radiation lights radiated from the fluorescence whitened sample when the fluorescence whitened sample is sequentially illuminated with a plurality of excitation lights Ik (k=1 to n) having different spectral power distributions and a spectral power distribution Id(λ) of the standard illumination light Id, wherein the first to third steps are as follows:

First step: Spectral power distributions Rf(Ik,λ) of fluorescence are obtained from the spectral power distributions R(Ik,λ) by respective excitation lights Ik;

Second step: The spectral power distributions Rf(Ik,λ) of fluorescence by the respective excitation lights Ik are linearly combined with a given weighting coefficient Wk, and an approximation R'f(Id,λ) of a spectral power distribution Rf(Id,λ) of fluorescence by the standard illumination light Id is obtained by following equation (6):

[Math. 1]

$$R'_f(I_d, \lambda) = \sum_k W_k \cdot R_f(I_k, \lambda);$$  Equation (6)

and

Third step: The approximation B'f(Id,λ) is obtained by following equation (7) from the approximation R'f(Id,λ) and the spectral power distribution Id(λ) of the standard illumination light Id

[Math. 2]

$$B'_f(I_d, \lambda) = \frac{R'_f(I_d, \lambda)}{I_d(\lambda)}$$  Equation (7)

2. The method for measuring the spectral radiation characteristics of the fluorescence whitened sample according to claim 1,
wherein the plurality of excitation lights Ik is monochromatic excitation lights.

3. The method for measuring the spectral radiation characteristics of the fluorescence whitened sample according to claim 2,
wherein the monochromatic excitation lights are monochromatic LED radiation lights.

4. The method for measuring the spectral radiation characteristics of the fluorescence whitened sample according to claim 1, comprising:
setting a plurality of sets of weighting coefficients Wk corresponding to a plurality of standard illumination lights Id, respectively; and
obtaining the approximation R'f(Id,λ) by applying a set of weighting coefficients Wk corresponding to each standard illumination light Id.

5. The method for measuring the spectral radiation characteristics of the fluorescence whitened sample according to claim 1,
wherein the plurality of excitation lights Ik includes a first type of excitation light Ik1 outside an overlapping range of a reflected light range and a fluorescence range, and a second type of excitation light Ik2 within the overlapping range,
at the first step, a spectral power distribution Rf(Ik1,λ) of fluorescence by the first type of excitation light Ik1 is obtained from a spectral power distribution R(Ik1,λ) of a sample radiation light by the first type of excitation light Ik1,
an approximation R'f(Ik2,λ) of at least a part of a spectral power distribution Rf(Ik2,λ) of fluorescence by the second type of excitation light Ik2 is estimated on the basis of the spectral power distribution R(Ik1,λ) of the sample radiation light by the first type of excitation light Ik1, and a remaining part is obtained from the spectral power distribution R(Ik2,λ) of the sample radiation light by the second type of excitation light Ik2.

6. The method for measuring the spectral radiation characteristics of the fluorescence whitened sample according to claim 5, comprising:
obtaining the approximation R'f(Ik2,λ) of at least a part of the spectral power distribution Rf(Ik2,λ) of fluorescence by the second type of excitation light Ik2 as the estimation at following fourth to sixth steps:

Fourth step: A ratio K of powers of the sample radiation lights by the first and second types of excitation lights Ik1 and Ik2 at one or more reference wavelengths λr1 outside the overlapping range is obtained by following equation (22):

[Math. 3]

$$K = \frac{R(I_{k2}, \lambda_{r1})}{R(I_{k1}, \lambda_{r1})}$$  Equation (22)

Fifth step: A correction coefficient C(λ) reflecting that a fluorescence wavelength λ is longer than an excitation wavelength μ is obtained; and Sixth step: The approximation R'f(Ik2,λ) is obtained by following equation (23) from the spectral power distribution R(Ik1,λ) of the sample radiation light by the first type of excitation light Ik1, the ratio K of the powers, and the correction coefficient C(λ)

[Math. 4]

$$R'_f(I_{k2},\lambda) = R(I_{k1},\lambda) \cdot K \cdot C(\lambda)$$  Equation (23).

7. The method for measuring the spectral radiation characteristics of the fluorescence whitened sample according to claim 6,
wherein the spectral power distribution of the second type of excitation light Ik2 is obtained from Ik2(μ), and the correction coefficient C(λ) is obtained by following equation (24):

[Math. 5]

$$C(\lambda) = 1 - \frac{\sum_{\mu=\lambda}^{\infty} I_{k2}(\mu)}{\sum_{\mu=0}^{\infty} I_{k2}(\mu)}$$  Equation (24)

8. The method for measuring the spectral radiation characteristics of the fluorescence whitened sample according to claim 5, wherein the part includes the overlapping range.

9. The method for measuring the spectral radiation characteristics of the fluorescence whitened sample according to claim 1,
wherein powers of the plurality of excitation lights Ik (k=1 to n) are proportional to the weighting coefficient Wk.

10. The method for measuring the spectral radiation characteristics of the fluorescence whitened sample according to claim 9,
wherein the powers of the plurality of excitation lights Ik (k=1 to n) are controlled by an irradiation time.

11. The method for measuring the spectral radiation characteristics of the fluorescence whitened sample according to claim 9,
wherein two or more excitation lights Ik out of the plurality of excitation lights Ik (k=1 to n) are simultaneously applied.

12. The method for measuring the spectral radiation characteristics of the fluorescence whitened sample according to claim 1,
wherein the weighting coefficient Wk for setting the powers of the plurality of excitation lights Ik (k=1 to n)

is obtained on the basis of a spectral power distribution Ik(μ) of the excitation light Ik obtained at most recent measurement.

13. The method for measuring the spectral radiation characteristics of the fluorescence whitened sample according to claim 12,
wherein each of the plurality of excitation lights Ik (k=1 to n) is a radiation light of a monochromatic LED driven at constant current, and
the spectral power distribution Ik(μ) of each of the plurality of excitation lights Ik is obtained on the basis of a forward voltage when driving the monochromatic LED and known correlation characteristics of forward voltage-spectral power distribution.

14. The method for measuring the spectral radiation characteristics of the fluorescence whitened sample according to claim 1, comprising:
setting the weighting coefficient Wk such that a spectral power distribution I'd(λ) of a synthetic excitation light I'd obtained by linearly combining the spectral power distributions of the plurality of excitation lights Ik by following equation (12) approximates the spectral power distribution Id(λ) of the standard illumination light Id

[Math. 6]

$$I'_d(\lambda) = \sum_k W_k \cdot I_k(\lambda) \qquad \text{Equation (12)}$$

15. The method for measuring the spectral radiation characteristics of the fluorescence whitened sample according to claim 1, comprising:
setting the weighting coefficient Wk at following seventh and eighth steps from
the spectral power distributions Ik(λ) of the plurality of excitation lights Ik,
the spectral power distribution Id(λ) of the standard illumination light Id, and
a plurality of different bispectral fluorescence emissivity coefficients FT(μ,λ) (T=1 to N, μ represents an excitation wavelength and λ represents a fluorescence wavelength), wherein the seventh and eighth steps are as follows:
Seventh step: Spectral power distributions Rf,T(Ik,λ) of fluorescence by the plurality of excitation lights Ik and a spectral power distribution Rf,T(Id,λ) of fluorescence by the standard illumination light Id are obtained by following equations (25) and (26) from the plurality of bispectral fluorescence emissivity coefficients FT(μ,λ), the spectral power distributions Ik(μ) of the plurality of excitation lights Ik, and a spectral power distribution Id(μ) of the standard illumination light Id

[Math. 7]

$$R_{f,T}(I_k,\lambda) = \int I_k(\mu) F_T(\mu,\lambda) d\mu \qquad \text{Equation (25)}$$

[Math. 8]

$$R_{f,T}(I_d,\lambda) = \int I_d(\mu) F_T(\mu,\lambda) d\mu \qquad \text{Equation (26);}$$

and
Eighth step: The weighting coefficient Wk is set such that a spectral power distribution R'f,T(Id,λ) of synthetic fluorescence obtained by linearly combining the spectral power distributions Rf,T(Ik,λ) of fluorescence by the plurality of excitation lights Ik by following equation (27) approximates the spectral power distribution Rf,T(Id,λ) of fluorescence by the standard illumination light Id for all of the plurality of bispectral fluorescence emissivity coefficients FT(μ,λ)

[Math. 9]

$$R'_{f,T}(I_d, \lambda) = \sum_k W_k \cdot R_{f,T}(I_k, \lambda) \qquad \text{Equation (27)}$$

16. The method for measuring the spectral radiation characteristics of the fluorescence whitened sample according to claim 1, comprising:
setting the weighting coefficient Wk at following ninth and tenth steps from
the spectral power distributions Ik(λ) of the plurality of excitation lights Ik,
the spectral power distribution Id(λ) of the standard illumination light Id, and
a plurality of different spectral quantum efficiencies FT(μ,λr2) (T=1 to N, μ represents an excitation wavelength) for fluorescence at a reference wavelength of λr2, wherein the ninth and tenth steps are as follows:
Ninth step: Fluorescence powers Rf,T(Ik,λr2) at the reference wavelength λr2 by the plurality of excitation lights Ik and fluorescence powers Rf,T(Id,λr2) at the reference wavelength λr2 by the standard illumination light Id are obtained by following equations (28) and (29) from the plurality of spectral quantum efficiencies FT(μ,λr2), the spectral power distributions Ik(μ) of the plurality of excitation lights Ik, and the spectral power distribution Id(μ) of the standard illumination light Id

[Math. 10]

$$R_{f,T}=(I_d,\lambda_{r2})=\int I_d(\mu) F_T(\mu,\lambda_{r2}) d\mu, \qquad \text{Equation (28)}$$

[Math. 11]

$$R_{f,T}=(I_k,\lambda_{r2})=\int I_k(\mu) F_T(\mu,\lambda_{r2}) d\mu, \qquad \text{Equation (29);}$$

and
Tenth step: The weighting coefficient Wk is set such that a synthetic fluorescence power R'f,T(Id,λr2) obtained by linearly combining the fluorescence powers Rf,T(Ik,λr2) by following equation (30) approximates the fluorescence power Rf,T(Id,λr2) by the standard illumination light Id for all of the plurality of spectral quantum efficiencies FT(μ,λr2)

[Math. 12]

$$R'_{f,T}(I_d, \lambda_{r2}) = \sum_k W_k \cdot R_{f,T}(I_k, \lambda_{r2}) \qquad \text{Equation (30)}$$

17. The method for measuring the spectral radiation characteristics of the fluorescence whitened sample according to claim 14,
wherein a part of the set weighting coefficients Wk is reset.

18. The method for measuring the spectral radiation characteristics of the fluorescence whitened sample according to claim 15,
wherein the bispectral fluorescence emissivity coefficients FT(μ,λ) of the fluorescence whitened sample to be measured are classified into a plurality of types, the plurality of different bispectral fluorescence emissivity coefficients being the plurality of types of bispectral fluorescence emissivity coefficients, or spectral quantum efficiencies FT($\mu$,$\lambda$r2) for fluorescence at the reference wavelength $\lambda$r2 of the fluorescence whitened sample to be measured are classified into a plurality of types, the plurality of different spectral quantum efficiencies being the plurality of types of spectral quantum efficiencies.

19. The method for measuring the spectral radiation characteristics of the fluorescence whitened sample according to claim 1, comprising:
    obtaining an approximation B'r($\lambda$) of a spectral reflectivity coefficient Br($\lambda$) from a spectral power distribution Ivis($\lambda$) of a measuring range illumination light Ivis having a power in an entire measuring range, and
    a spectral power distribution Rr(Ivis,$\lambda$) of a sample reflected light by the measuring range illumination light Ivis, and
    obtaining an approximation B't(Id,$\lambda$) of a total spectral emissivity coefficient Bt(Id,$\lambda$) by the standard illumination light Id by a sum of the approximation B'r($\lambda$) and the approximation B'f(Id,$\lambda$).

20. The method for measuring the spectral radiation characteristics of the fluorescence whitened sample according to claim 5, comprising:
    obtaining a spectral reflectivity coefficient Br($\lambda$) outside the overlapping range from a spectral power distribution Ivis1($\lambda$) of an illumination light Ivis1 outside the overlapping range having a power in the entire measuring range outside the overlapping range and a spectral power distribution Rr(Ivis1,$\lambda$) of a sample reflected light by the illumination light Ivis1 outside the overlapping range;
    providing an approximation B''t(Id,$\lambda$) of a total spectral emissivity coefficient outside the overlapping range by the standard illumination light Id by a sum of the spectral reflectivity coefficient Br($\lambda$) and the approximation B'f(Id,$\lambda$); and
    obtaining the approximation B''t(Id,$\lambda$) of the total spectral emissivity coefficient of the overlapping range by the standard illumination light Id by a sum of a total spectral emissivity coefficient Bt(Id2,$\lambda$) of the overlapping range by the overlapping range illumination light Id2 obtained from a spectral power distribution Id2($\lambda$) of an overlapping range illumination light Id2 having a spectral power distribution approximating the standard illumination light Id in the overlapping range and a spectral power distribution R(Id2,$\lambda$) of a sample radiation light by the overlapping range illumination light Id2,
    and a fluorescence spectral emissivity coefficient Bf(Id1,$\lambda$) by an excitation component Id1 other than an overlapping range component of the standard illumination light Id.

21. The method for measuring the spectral radiation characteristics of the fluorescence whitened sample according to claim 20,
    wherein the overlapping range illumination light Id2 having a spectral power distribution approximating the standard illumination light Id in the overlapping range is provided by weighted linear combination of a plurality of illumination lights.

22. The method for measuring the spectral radiation characteristics of the fluorescence whitened sample according to claim 21,
    wherein at least one of the plurality of illumination lights is any of the plurality of excitation lights Ik.

23. The method for measuring the spectral radiation characteristics of the fluorescence whitened sample according to claim 20,
    wherein the Bf(Id1,$\lambda$) being a component not by the overlapping range illumination light Id2 of the approximation B'f(Id,$\lambda$) is obtained at following eleventh and twelfth steps:
    Eleventh step: A power coefficient A is obtained by following equation (21) from a total spectral emissivity coefficient Bt(Id2,$\lambda$r3) by the overlapping range illumination light Id2 at one or more reference wavelengths $\lambda$r3 not affected by a reflected light of the overlapping range illumination light Id2, and an approximation B'f(Id,$\lambda$r3) of a fluorescence emissivity coefficient by the standard illumination light Id

[Math. 13]
$$A = 1 - \frac{B_t(I_{d2}, \lambda_{r3})}{B'_f(I_d, \lambda_{r3})} \qquad \text{Equation (21)}$$

and
    Twelfth step: The Bf(Id1,$\lambda$) is obtained by following equation (35) from the approximation B'f(Id,$\lambda$) of the fluorescence spectral emissivity coefficient by the standard illumination light Id, and the power coefficient A

[Math. 14]
$$B_f(I_{d1},\lambda) = A \cdot B'_f(I_d,\lambda) \qquad \text{Equation (35)}.$$

24. The method for measuring the spectral radiation characteristics of the fluorescence whitened sample according to claim 19, comprising:
    obtaining the spectral power distribution Rr(Ivis,$\lambda$) of the sample reflected light by subtracting a spectral power distribution Rf(Ivis,$\lambda$) of fluorescence by the measuring range illumination light Ivis from a spectral power distribution R(Ivis,$\lambda$) of a sample radiation light by the measuring range illumination light Ivis.

25. The method of measuring the spectral radiation characteristics of the fluorescence whitened sample according to claim 24,
    wherein the measuring range illumination light Ivis is formed of a first measuring range illumination light Ivis1 not including an excitation range and a second measuring range illumination light Ivis2 including the excitation range, and
    the approximation B'r($\lambda$) of the spectral reflectivity coefficient Br($\lambda$) of the fluorescence whitened sample is obtained by following thirteenth to sixteenth steps from a spectral power distribution Ivis1($\lambda$) of the first measuring range illumination light Ivis1 and a spectral power distribution R(Ivis1,$\lambda$) of the sample radiation light by the first measuring range illumination light, and
    a spectral power distribution Ivis2($\lambda$) of the second measuring range illumination light Ivis2 and a spectral power distribution R(Ivis2,$\lambda$) of the sample radiation light by the second measuring range illumination light,
    wherein the thirteenth to sixteenth steps are as follows:
    Thirteenth step: The spectral power distribution Ivis($\lambda$) of the measuring range illumination light Ivis is provided by a sum of the spectral power distributions Ivis1($\lambda$) and Ivis2($\lambda$) of the first and second measuring range illumination lights;

Fourteenth step: The spectral power distribution R(Ivis,λ) of the sample radiation light by the measuring range illumination light Ivis is provided by a sum of R(Ivis1,λ) and R(Ivis2,λ) by the first and second measuring range illumination lights;

Fifteenth step: A spectral power distribution Rf(Ivis2,λ) of fluorescence by the second measuring range illumination light Ivis2 is obtained; and Sixteenth step: The approximation B'r(λ) is obtained by following equation (31) while setting the Rf(Ivis2,λ) as Rf(Ivis,λ)

[Math. 15]

$$B'_r(\lambda) = \frac{R(I_{VIS}, \lambda) - R_f(I_{VIS}, \lambda)}{I_{VIS}(\lambda)} \qquad \text{Equation (31)}$$

26. The method for measuring the spectral radiation characteristics of the fluorescence whitened sample according to claim 25, comprising:
    obtaining the spectral power distribution Rf(Ivis2,λ) of fluorescence by the second measuring range illumination light at following seventeenth to twentieth steps from the spectral power distribution Ivis2(λ) of the second measuring range illumination light, the spectral power distribution R(Ivis2,λ) of the sample radiation light by the second measuring range illumination light, the spectral power distribution Ik1(λ) of the first type of excitation light outside the overlapping range of the reflected light range and the fluorescence range, and the spectral power distribution R(Ik1,λ) of the sample radiation light by the first type of excitation light, wherein the seventeenth to twentieth steps are as follows:
    Seventeenth step: A component outside the overlapping range of the spectral power distribution Rf(Ivis2,λ) of fluorescence by the second measuring range illumination light is obtained from the spectral power distribution R(Ivis2,λ) of the sample radiation light by the second measuring range illumination light;
    Eighteenth step: A ratio K' between a spectral power distribution R(Ik1,λr4) of the sample radiation light by the first type of excitation light and a spectral power distribution R(Ivis2,λr4) of the sample radiation light by the second measuring range illumination light at one or more reference wavelengths λr4 outside the overlapping range is obtained by following equation (32);

[Math. 16]

$$K' = \frac{R(I_{VIS2}, \lambda_{r4})}{R(I_{k1}, \lambda_{r4})} \qquad \text{Equation (32)}$$

Nineteenth step: A correction coefficient C'(λ) reflecting that the fluorescence wavelength λ is longer than the excitation wavelength μ is obtained; and Twentieth step: An approximation R'f(Ivis2,λ) of a component in the overlapping range of the spectral power distribution Rf(Ivis2,λ) of fluorescence by the second measuring range illumination light is obtained by following equation (33) from the spectral power distribution R(Ik1,λ) of the sample radiation light by the first type of excitation light, the power ratio K', and the correction coefficient C'(λ)

[Math. 17]

$$R'_f(I_{VIS2}, \lambda) = R(I_{k1}, \lambda) \cdot K' \cdot C'(\lambda) \qquad \text{Equation (33)}.$$

27. The method for measuring the spectral radiation characteristics of the fluorescence whitened sample according to claim 26,
    wherein the correction coefficient C'(λ) is obtained from the spectral power distribution Ivis2(λ) of the second measuring range illumination light by following equation (34):

[Math. 18]

$$C'(\lambda) = 1 - \frac{\sum_{\mu=\lambda}^{\infty} I_{VIS2}(\mu)}{\sum_{\mu=0}^{\infty} I_{VIS2}(\mu)} \qquad \text{Equation (34)}$$

28. A device for measuring a spectral radiation characteristics of a fluorescence whitened sample, comprising
    a plurality of excitation light illuminators for illuminating the fluorescence whitened sample with a plurality of excitation lights Ik (k=1 to n) having different spectral power distributions;
    a sample radiation light spectroscopic part for measuring spectral power distributions R(Ik,λ) of sample radiation lights being radiation lights radiated from the fluorescence whitened sample illuminated by the excitation lights Ik; and
    a hardware processor,
    wherein the hardware processor sequentially lights up the plurality of excitation light illuminators to allow the sample radiation light spectroscopic part to measure the spectral power distributions R(Ik,λ) of the sample radiation lights,
    obtains spectral power distributions Rf(Ik,λ) of fluorescence from the spectral power distributions R(Ik,λ) of the sample radiation lights,
    obtains an approximation R'f(Id,λ) of a spectral power distribution Rf(Id,λ) of fluorescence by a standard illumination light Id by using the spectral power distributions Rf(Ik,λ) of fluorescence and a given weighting coefficient Wk by following equation (6):

[Math. 19]

$$R'_f(I_d, \lambda) = \sum_k W_k \cdot R_f(I_k, \lambda); \qquad \text{Equation (6)}$$

and
    obtains an approximation B'f(Id,λ) of a fluorescence spectral emissivity coefficient Bf(Id,λ) by the standard illumination light Id from the approximation R'f(Id,λ) and a known spectral power distribution Id(λ) of the standard illumination light Id by following equation (7):

[Math. 20]

$$B'_f(I_d, \lambda) = \frac{R'_f(I_d, \lambda)}{I_d(\lambda)} \qquad \text{Equation (7)}$$

29. The device for measuring the spectral radiation characteristics of the fluorescence whitened sample according to claim 28,
wherein each of the plurality of excitation lights Ik is a radiation light of a monochromatic LED.

30. The device for measuring the spectral radiation characteristics of the fluorescence whitened sample according to claim 28, further comprising:
an excitation light spectroscopic part,
wherein the hardware processor allows the excitation light spectroscopic part to measure the spectral power distributions Ik($\lambda$) of the excitation lights Ik, and obtains the weighting coefficient Wk on the basis of the spectral power distributions Ik($\lambda$).

31. The device for measuring the spectral radiation characteristics of the fluorescence whitened sample according to claim 29, further comprising:
a driver which drives the monochromatic LED at a constant current; and
a forward voltage measuring part which measures a forward voltage of the monochromatic LED at the time of driving,
wherein the hardware processor estimates the spectral power distributions Ik($\lambda$) of the excitation lights Ik on the basis of the forward voltage measured by the forward voltage measuring part, and
obtains the weighting coefficient Wk on the basis of the estimated spectral power distributions Ik($\lambda$).

32. The device for measuring the spectral radiation characteristics of the fluorescence whitened sample according to claim 29, further comprising:
a measuring range illuminator which illuminates the fluorescence whitened sample with a measuring range illumination light Ivis having a power in an entire measuring range,
wherein the hardware processor lights up the measuring range illuminator to allow the sample reflected light spectroscopic part to measure a spectral power distribution Rr(Ivis,$\lambda$) of a sample radiation light by the measuring range illumination light,
obtains an approximation B'r($\lambda$) of a spectral reflectivity coefficient Br($\lambda$) from a spectral power distribution Ivis($\lambda$) of the measuring range illumination light and the spectral power distribution Rr(Ivis,$\lambda$) of the sample reflected light, and
obtains an approximation B't(Id,$\lambda$) of a total spectral emissivity coefficient Bt(Id,$\lambda$) by the standard illumination light by a sum of the approximation B'r($\lambda$) and the approximation B'f(Id,$\lambda$) of the fluorescence spectral emissivity coefficient Bf(Id,$\lambda$) by the standard illumination light.

33. The device for measuring the spectral radiation characteristics of the fluorescence whitened sample according to claim 32,
wherein the measuring range illuminator includes a blue-excited white LED and one or more monochromatic LEDs having a power in a measuring range where the blue-excited white LED does not have power, and the measuring range illumination light Ivis is formed of a radiation light of the blue-excited white LED and a radiation light of the one or more monochromatic LEDs.

34. The device for measuring the spectral radiation characteristics of the fluorescence whitened sample according to claim 32,
wherein the measuring range illuminator includes a white light source, a fluorescence excitation wavelength band cut filter, and one or more monochromatic LEDs having a power in a fluorescence excitation light wavelength band, and the measuring range illumination light Ivis is formed of a radiation light of the white light source passing through the fluorescence excitation wavelength band cut filter and a radiation light of the one or more monochromatic LEDs.

* * * * *